United States Patent
Marsh et al.

(10) Patent No.: US 10,918,799 B2
(45) Date of Patent: Feb. 16, 2021

(54) DRIVE MECHANISM AND DRUG DELIVERY DEVICE HEREWITH

(71) Applicant: Sanofi, Paris (FR)

(72) Inventors: William Geoffrey Arthur Marsh, Buckinghamshire (GB); Matthew Meredith Jones, Warwick (GB)

(73) Assignee: Sanofi, Paris (FR)

( * ) Notice: Subject to any disclaimer, the term of this patent is extended or adjusted under 35 U.S.C. 154(b) by 707 days.

(21) Appl. No.: 15/532,795

(22) PCT Filed: Dec. 8, 2015

(86) PCT No.: PCT/EP2015/078903
§ 371 (c)(1),
(2) Date: Jun. 2, 2017

(87) PCT Pub. No.: WO2016/091841
PCT Pub. Date: Jun. 16, 2016

(65) Prior Publication Data
US 2017/0340834 A1   Nov. 30, 2017

(30) Foreign Application Priority Data
Dec. 8, 2014   (EP) .................................... 14306962

(51) Int. Cl.
*A61M 5/315* (2006.01)
*A61M 5/24* (2006.01)
(Continued)

(52) U.S. Cl.
CPC .......... *A61M 5/31511* (2013.01); *A61M 5/24* (2013.01); *A61M 5/2422* (2013.01);
(Continued)

(58) Field of Classification Search
CPC .... A61M 5/24; A61M 5/2422; A61M 5/3157; A61M 2005/31518; A61M 2005/3152;
(Continued)

(56) References Cited

U.S. PATENT DOCUMENTS 5,947,934 A * 9/1999 Hansen ............. A61M 5/31525
604/187
6,074,372 A   6/2000 Hansen
(Continued)

FOREIGN PATENT DOCUMENTS

| CN | 1980705 | 6/2007 |
|---|---|---|
| CN | 1225024 | 8/2019 |

(Continued)

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.
(Continued)

*Primary Examiner* — Shefali D Patel
(74) *Attorney, Agent, or Firm* — Fish & Richardson P.C.

(57) ABSTRACT

The present disclosure is generally directed to a drive mechanism for use in a drug delivery device having a cylindrical cartridge, i.e. a handheld injection device for selecting and dispensing a number of user variable doses of a medicament. The drive mechanism includes a base element, a toothed piston rod, which is guided within and movable relative to the base element, and a drive gear having a pinion, which is rotatably held in the base element and in meshed engagement with the toothed piston rod. The toothed piston rod includes multiple rigid rod pieces which are connected by hinges. The rigid rod pieces comprise a flat plate provided with a straight toothed rack.

15 Claims, 8 Drawing Sheets

Specification includes a Sequence Listing.

(51) Int. Cl.
*A61M 5/31* (2006.01)
*A61M 5/20* (2006.01)

(52) U.S. Cl.
CPC ........ *A61M 5/3157* (2013.01); *A61M 5/3158* (2013.01); *A61M 5/31536* (2013.01); *A61M 5/31541* (2013.01); *A61M 5/31548* (2013.01); *A61M 5/31553* (2013.01); *A61M 5/31558* (2013.01); *A61M 5/31575* (2013.01); *A61M 5/31581* (2013.01); *A61M 5/31583* (2013.01); *A61M 5/31585* (2013.01); *A61M 5/2033* (2013.01); *A61M 5/31515* (2013.01); *A61M 5/31535* (2013.01); *A61M 2005/3126* (2013.01); *A61M 2005/3152* (2013.01); *A61M 2005/3154* (2013.01); *A61M 2005/31508* (2013.01); *A61M 2005/31518* (2013.01); *A61M 2205/581* (2013.01); *A61M 2205/582* (2013.01); *A61M 2205/585* (2013.01); *A61M 2207/00* (2013.01); *A61M 2207/10* (2013.01)

(58) Field of Classification Search
CPC ...... A61M 2205/581; A61M 2205/582; A61M 5/31501; A61M 5/31511; A61M 5/31535; A61M 5/31536; A61M 5/31548; A61M 5/3155; A61M 5/31553; A61M 5/31558; A61M 5/31575; A61M 5/3158; A61M 5/31581; A61M 5/31583; A61M 5/31585; A61M 2005/3125; A61M 2005/3126; A61M 2005/31508; A61M 2005/31541
See application file for complete search history.

(56) References Cited

U.S. PATENT DOCUMENTS 6,582,404 B1   6/2003   Klithaard et al.
6,692,472 B2 *   2/2004   Hansen .................. A61M 5/20
                                                                 604/210

FOREIGN PATENT DOCUMENTS

| EP | 1250167 | 7/2005 |
|---|---|---|
| WO | WO 98/01173 | 6/1997 |
| WO | WO 01/83008 | 11/2001 |
| WO | WO 2004/007002 | 1/2004 |
| WO | WO 2004/078241 | 9/2004 |
| WO | WO 2006/003130 | 1/2006 |
| WO | WO 2012/089445 | 7/2012 |
| WO | WO-2013156224 A1 * | 10/2013 |
| WO | WO 2014/052676 | 4/2014 |
| WO | WO-2014052676 A1 * | 4/2014 |
| WO | WO 2014/166905 | 10/2014 |
| WO | WO 2016/091841 | 6/2016 |

OTHER PUBLICATIONS

International Preliminary Report on Patentability in International Application No. PCT/EP2015/078903, dated Jun. 13, 2017, 6 pages.
International Search Report and Written Opinion in International Application No. PCT/EP2015/078903, dated Feb. 16, 2016, 9 pages.

* cited by examiner

Figure 13
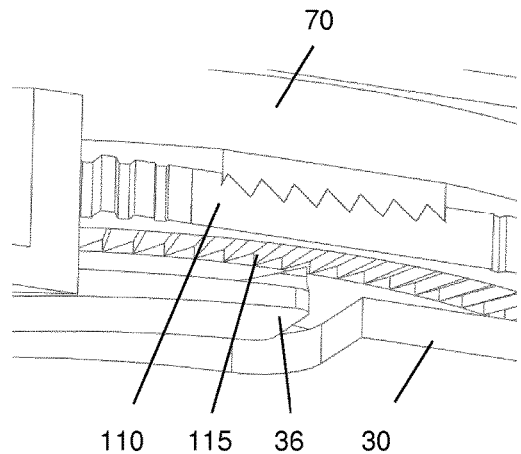
Figure 14a
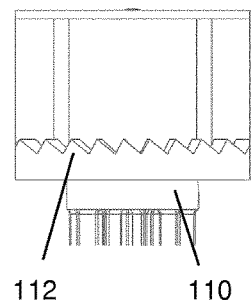
Figure 14b
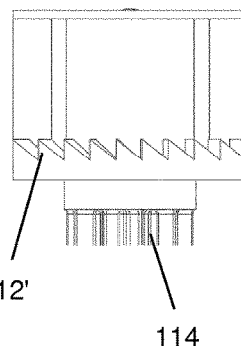
Figure 15
Figure 16
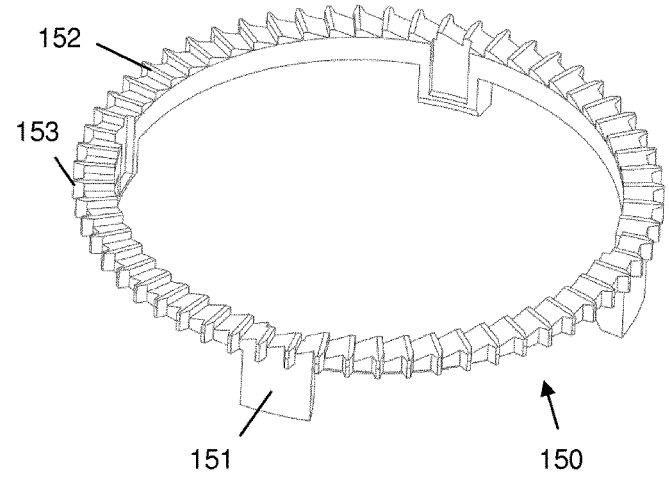
Figure 17
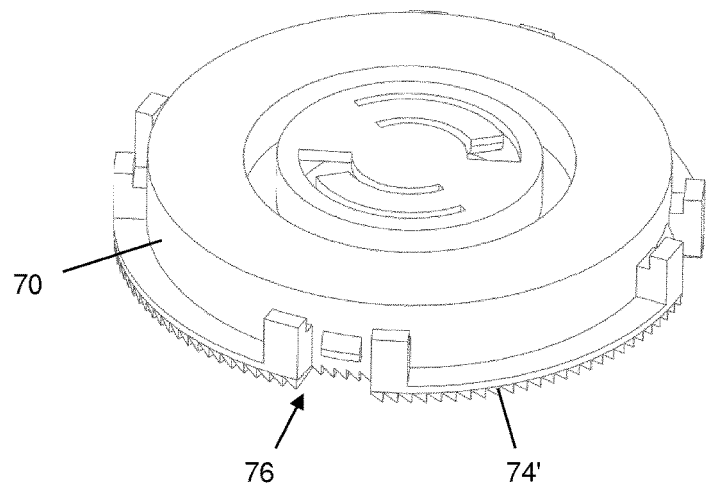

DRIVE MECHANISM AND DRUG DELIVERY DEVICE HEREWITH

CROSS-REFERENCE TO RELATED APPLICATIONS

This application is a U.S. national stage application under 35 USC § 371 of International Application No. PCT/EP2015/078903, filed on Dec. 8, 2015, which claims priority to European Patent Application No. 14306962.3, filed on Dec. 8, 2014, the entire contents of which are incorporated herein by reference.

TECHNICAL FIELD

The present disclosure is generally directed to a drive mechanism for use in a drug delivery device, i.e. a handheld injection device for selecting and dispensing a number of user variable doses of a medicament.

BACKGROUND

Drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable drug delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is in general applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. Further types of energy storage may comprise compressed fluids or electrically driven devices with a battery or the like. Although many aspects of the present disclosure are applicable for all of these types of devices, i.e. for devices with or without a drive spring or the like energy storage, the preferred embodiments require some kind of energy storage.

These types of delivery devices generally comprise of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the device that is used to set (select) a dose. During an injection, a plunger or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

The dosing section of drug delivery devices for selecting and dispensing a number of user variable doses of a medicament often comprises a display for indicating the selected dose to a user. This is especially important where a user may select a different dose each time depending on the state of health. There are mechanical displays, e.g. a drum with printed numbers on its outer surface, wherein the number corresponding to the actually selected dose is visible through a window or opening in the device. Although such mechanical displays are simple and reliable, they usually require a relatively large construction space which makes the devices bulky. In addition, the size of the numbers is in some cases too small for visually impaired users. Further, electronic displays are known, e.g. LCD displays, which have the benefit of a relatively large number size without requiring too much construction space. However, a downside of electronic displays is that they require an energy source and that such electronic components may be too expensive, especially in a disposable drug delivery device.

A disposable drug delivery device is known from WO 2004/078241 A1, wherein the display comprises a number sleeve with numbers printed on its outer surface. The device further comprises a housing, a cartridge holder for retaining a cartridge containing a medicament, a piston rod displaceable relative to the cartridge holder, a driver coupled to the piston rod, a dose setting knob coupled to the driver and fixed to the number sleeve, and an injection button. The number sleeve is in threaded engagement with the housing, such that the number sleeve rotates along a helical path in a first direction during dose selecting and rotates back into the housing in a second, opposite direction during dose dispensing.

An alternative design of the display is known for example from EP 1 250 167 B1, which shows a drug delivery device with a display similar to an egg-timer. A dose setting element is provided rotatable about an axis which is perpendicular to the longitudinal axis of the cartridge. The number display is arranged as a ring having respective markings with a pointer tip on the dose setting element pointing at the set dose marking. A downside of this display is that only every five number is indicated as a figure with dashes for every single unit. This makes it difficult to read the exact dose. Further, it may be difficult to identify the exact position of the pointer tip, which again raises the risk of a misreading.

U.S. Pat. No. 5,947,934 mentions the use of a flexible piston rod in an injection syringe without indicating details regarding the design of the piston rod or its interaction with other component parts.

U.S. Pat. No. 6,074,372 refers to an injection syringe with an elongate straight piston rod having a toothed part which engages barbs of a dose administration wheel. A further example of a flexible piston rod with a cogging engaging a pinion is given in U.S. Pat. No. 6,582,404.

WO 98/01173 A1 refers to a flexible piston rod and a rack and pinion drive mechanism. A first embodiment of WO 98/01173 A1 discloses a piston rod formed by a tape-like flexible rack. A second embodiment comprises multiple rigid rod pieces connected by hinges. The rigid rod pieces are each provided with curved racks. Supporters provided on the opposite side of the racks fit into the cartridge interior to guide the piston rod within the cartridge. It is proposed to drive such a piston rod either by a force applied to the rod end opposite to the cartridge, which requires guiding the rod over its entire length or by a pinion with the piston rod looping around the pinion.

Both alternatives result in constraints regarding the design and location of a drive mechanism within a drug delivery device. In addition, the flexural stiffness may require improvement depending on the application of the device.

Further flexible piston rods with rigid toothed rod pieces connected to each other by hinges are known from WO 01/83008 A1 and WO 2012/089445 A1.

SUMMARY

The present disclosure is not directed to so called fixed dose devices which only allow dispensing of a predefined dose without the possibility to increase or decrease the set dose.

The present disclosure provides an improved drive mechanism and drug delivery device with reduced frictional forces allowing a wider freedom of design choices.

A drive mechanism according to the disclosure is suitable for use in a drug delivery device with a cylindrical cartridge and comprises a base element or chassis, a toothed piston rod, which is guided within and movable relative to the base portion or chassis, and a drive gear having a pinion, which is rotatably held in the base element or chassis and in meshed engagement with the toothed piston rod. The toothed piston rod comprises multiple rigid rod pieces which are connected by hinges, for example integral hinges, such that the rigid rod pieces are arranged in a swivelling manner one behind the other. The rigid rod pieces each comprise a flat plate provided with a straight toothed rack. In other words, neither the rigid rod pieces nor the toothed racks are curved or cambered. This increases the flexural stiffness of the rod and allows use of the rod in a rack and pinion application not requiring that the rod loops around a pinion. Thus, there are more design options for the location and arrangement of the rod and the pinion within a drive mechanism and/or within a drug delivery device. In addition, the pinion may be relatively small, which is not possible when the rod is intended to loop around the pinion.

Typically, the flexible piston rod is located within the base element or chassis and engages, via a rack and pinion interface, the drive gear so that rotation of the drive gear advances the piston rod. When used in a drug delivery device with a cartridge having a bung, the distal end of the piston rod acts on the bung within the liquid medicament cartridge, which expels medicament from the cartridge during dose dispensing by the advancement of the piston rod.

The flexible piston rod is a single component with discrete segments (rigid rod pieces) connected together by thin sections of material which form flexible hinges. The flexibility in bending permits a significantly shorter device format whilst using a conventional glass medicament cartridge.

In a preferred embodiment of the disclosure, the end faces of the segments are planar and, when the flexible piston rod is straightened, the adjacent segment faces abut each other, allowing the component to withstand a compressive load. Together with the design of the segments as flat plates, this contributes to the flexural stiffness of the rod. The flexible piston rod may be restrained within the base element or chassis to maintain the flexed state and prevent the rack gear teeth from disengaging from the pinion of the drive gear. As the piston rod is advanced, via the rack and pinion engagement with the drive gear, the trailing segments of piston rod are drawn into engagement with the drive gear pinion. The subsequent segments drive the preceding segments, loading them in compression, and apply a force to the bung. As the flexible piston rod advances, the first segment may move out of the support provided by the base element or chassis. Without additional support it is likely that the piston rod would buckle under this compressive loading. The additional support to prevent buckling is created by the inner wall of the cartridge providing constraint to the outer surfaces of the flexible piston rod.

The base element or chassis is a rigid component part, which is typically fixed within a device housing or is a part thereof. The base element or chassis is the (immovable) reference for relative movements of the piston rod, the drive gear or further component parts of the drive mechanism or the drug delivery device.

According to an embodiment of the disclosure, the base element or chassis comprises a first curved guiding section and a second straight guiding section with the drive gear and/or its pinion being arranged protruding into or adjacent to the second straight guiding section. In other words, the meshing engagement between the pinion and the rod segments occurs in the straight guiding section. Thus, the design of the curved guiding section has not to be adapted to allow engagement of the pinion and the rod but may have a form suitable to optimize the available space for storing the flexible piston rod. This drive mechanism allows the design of a relatively compact drug delivery device.

In addition, the base element or chassis may comprise a receiving section for retaining the cartridge. Typically, the receiving section is arranged adjacent to the second straight guiding section such that the rod enters the cartridge shortly after the pinion. The second straight guiding section may lead into or merge into the receiving section.

To further increase the flexural stiffness of the rod, the flat plate of each segment or rod piece may comprise a flange located on the opposite side of the straight toothed rack. The end faces of the flanges are preferably planar and, when the flexible piston rod is straightened, the adjacent flange faces abut each other, allowing the component to withstand a compressive load. The length of the flanges is preferably adapted to the dimensions of the cartridge such that the flanges (in addition to the plates) guide the rod within the cartridge.

In a preferred embodiment the base element or chassis has a generally circular configuration with the pinion being located at the center of the base element wherein the first curved guiding section and the second straight guiding section are located offset from the center of the base element. This may contribute in reducing the overall dimensions of the drug delivery device using this drive mechanism.

Further, the drive mechanism may comprise a clutch provided by a splined portion of the drive gear and a corresponding splined portion of the base element. Preferably, the drive gear is axially movable along its rotational axis between a first position, typically a dose setting or dose correcting position, in which the drive gear is rotationally constrained to the base element by engagement of the clutch and a second position, typically a dose dispensing position, in which the clutch is disengaged and relative rotation between the base element and the drive gear is allowed. This prevents unintended movement of the piston rod during dose setting or dose correction. In addition, this constraint may be used to react a force or torque of an optional drive spring.

According to a further development of this idea, the drive mechanism may comprise a compression spring interposed between the base element and the drive gear. Preferably, the spring biases the drive gear into its first position relative to the base element. In other words, the drive gear and the base element or chassis are decoupled by relative movement of the drive gear and the base element or chassis against the force of the spring.

In a preferred embodiment of the disclosure the drive mechanism further comprises a drive spring. This may be a spring which is charged during dose setting, i.e. a spring storing energy applied by a user, or a spring pre-strained during manufacture or assembly of the mechanism or a combination thereof. Preferably, the drive spring is fixed to the base element or chassis (or any other housing component) with one end and, at least when the drive gear is allowed to rotate relative to the base element, exerts a force or torque to the drive gear for rotating the drive gear relative to the base element, which rotation results in a movement of the toothed piston rod. The spring may be directly attached to the drive gear, e.g. if the spring is charged for the whole intended life of the mechanism during manufacture or assembly. As an alternative, the spring may be attached to a component part which is (directly or indirectly) coupled to the drive gear for dose dispensing.

The use of a drive spring or the like energy storage has the benefit of reducing the user force required to expel the contents of the cartridge. A pre-strained spring has the further advantage to reduce the force required during dose setting. As an alternative to a pre-strained spring, a spring or other suitable power reservoir may be used, which is charged or strained during dose setting. Another benefit of devices where the force required to expel the contents of the cartridge is provided by a power reservoir instead of the user is that a dial extension of the device may be avoided, which means that the size of the device remains the same irrespective of whether a dose is set or the amount of the set dose. This makes the device more compact and user-friendly.

A drug delivery device according to the disclosure comprises a drive mechanism as defined above. The device may further comprise a dose setting member for setting user variable doses of a medicament, a display for indicating the dose set by the dose setting member and at least one coupling member interposed between the drive gear and the dose setting member and/or the display. Typically, the coupling member is arranged such that relative rotation between the drive gear and the dose setting member is allowed during dose setting. For example, the coupling member may rotate together with the dose setting member and/or the display during dose setting while the drive gear is rotationally constrained to the base element. During dose dispensing the coupling member, the dose setting member and/or the display may be rotationally constrained to the drive gear.

In addition, the drug delivery device may comprise a housing, which is rigidly fixed with the base element or chassis, e.g. by permanent attachment or as an integral part thereof. The housing may have a longitudinal axis defined by a compartment for receiving the cartridge, e.g. the cartridge receiving section of the drive mechanism, wherein the dose setting member is arranged rotatable within the housing with its axis of rotation being perpendicular to the longitudinal axis of the housing. This allows an ergonomic design of the drug delivery device.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring force needed for dispensing very high doses, while still being suitable for a wide range of patients needing different dose sizes. Preferably, the limits for the minimum dose and the maximum dose are provided by hard stop features. For example, the rotation of the dose setting member relative to the housing is limited by rotational stops defining a minimum dose position and a maximum dose position. The minimum dose stop has to be robust enough to withstand the load exerted by the power reservoir via the retaining member. The rotation of the dose setting member, the coupling element and/or the display or number wheel may be limited by rotational stops defining a minimum dose position and a maximum dose position. The minimum dose position and the maximum dose position may be defined by rotational hard stops provided on the housing and e.g. the number wheel of the display. Preferably, the same protrusions define a minimum dose position and a maximum dose position, i.e. the relative rotation between the minimum and maximum dose stop is limited to nearly 360°.

The drug delivery device may further comprise a trigger being axially movable in the direction of the axis of rotation of the dose setting member, i.e. perpendicular to the longitudinal axis of the housing. Actuation of the trigger typically results in an axial movement of the drive gear for rotationally decoupling the drive gear and the base element.

According to a further embodiment of the present disclosure the device comprises clicker components. Different clicker mechanisms may be active during dose setting and dose dispensing. For example, a dose setting feedback may be generated by a ratchet provided between the coupling element and the drive gear wherein re-engagement of ratchet teeth generates a feedback signal. A dose dispensing feedback may be generated between the base element or chassis and the drive gear. For example, a clicker arm in the form of a compliant cantilever beam integrated in the chassis interfaces axially with ratchet features on the drive gear. To provide an additional non-visual, i.e. an audible and/or tactile, feedback to a user only at the end of dispensing of a set dose, a clicker may be provided by the chassis and the coupling member which is active as the device returns to its minimum dose stop. To differentiate between these feedback signals, the end of dose dispensing feedback, which is generated only at the end of dispensing of a set dose, is distinct from the further feedback(s). For example, a different sound may be generated. Preferably, the end of dose dispensing feedback mechanism comprises a ramp feature on one of the base element and the coupling member and a flexible clicker arm on the other of the base element and the coupling member. The coupling member may be axially movable along the axis of rotation of the dose setting member between a dose setting and dose correcting position and a dose dispensing position. This prevents the ramp and the clicker arm from interacting during dose correction (reducing a set dose). In this context, end of dose dispensing shall mean the moment, when the piston rod has completed its advancement corresponding to the set dose. Thus, due to the elasticity of the cartridge bung, liquid may still be expelled shortly after the end of dose dispensing.

In addition to the non-visual feedbacks, drug delivery devices usually have a display indicating the actually set dose. For example, a number wheel may be arranged coaxially with and rotationally coupled to the dose setting member with a series of markings being provided on the outer circumference of the number wheel. A preferred embodiment of the disclosure is based on the idea to provide a series of markings on the outer circumference of a number wheel of the display and to deviate the image of the markings of the number wheel, preferably by 90°, by means of a prism. The outer circumference of a wheel is an area having enough space to arrange the series of markings with every single figure illustrated, or with every second figure illustrated and a line to mark intermediate positions. On the other hand, as the outer circumference of a wheel might not be the most convenient position of the markings to be readable by a user during dose setting and during dispensing, deviation is provided to increase ease of use.

Regarding the direction of the deviation, it is convenient for some users if the display faces in the direction in which actuation is required during dose setting and/or dose dispensing. For example, if rotation in a plane is required for dose setting and pushing a trigger perpendicular to said plane is required for dose dispensing the display may be arranged next to this plane. Preferably, the number wheel is rotatable about an axis, wherein the prism is arranged such that the image of the markings of the number wheel is deviated in a direction parallel to said axis. According to a preferred embodiment, the at least one prism is a triangular prism, and the series of markings is provided reversed (mirrored) on the outer circumference of the number wheel to be readable through the prism. As an alternative, a penta-prism may be used instead of a simple (triangular) prism allowing the transmission of an image through a right angle without inverting it, that is, without changing the image's handedness. Thus, the series of markings is provided non-mirrored on the outer circumference of the number wheel.

Preferably, the surface of the prism is designed to provide a magnification of the markings on the number wheel. This allows it even with limited space available on the outer circumferential surface of the number wheel to provide an individual figure for every unit (or every second unit) of dose to be set which still is conveniently readable by a user.

According to a further aspect of the present disclosure, the drive mechanism further comprises a nut which is guided axially displaceable and non-rotatable with respect to one of the drive gear and the coupling member. For example, the nut is rotationally coupled to the drive gear, via a splined interface. It moves along a helical path relative to the coupling member, via a threaded interface, when relative rotation occurs between the coupling member and drive gear (i.e. during dialing). The nut moves towards an end stop, wherein the nut and the end stop may be provided in the drive mechanism of the injection device such that the nut prevents setting of a dose exceeding the (dispensable) amount of a medicament in the injection device. In other words, the end stop preferably defines the length of a track on which the nut travels during dose setting, wherein the length of the track corresponds to the total (dispensable) amount of medicament in the cartridge.

The coupling member of the drug delivery device may be a single component part in the form of a dial gear which is rotationally coupled to the display (e.g. the number wheel) via a splined interface that permits relative axial movement between the dial gear and number wheel. In a preferred embodiment, the drive gear is axially constrained between the chassis and dial gear and biased away from the chassis by the compression spring, which is also the trigger spring. The drive gear is rotationally coupled to the dial gear via a detent and clutch interface, which occurs on an axial abutment. It is preferably possible to overhaul this ratchet, which provides a detented position between the dial gear and the drive gear corresponding to each dose unit, and engages different ramped tooth angles during clockwise (CW) and counter clockwise (CCW) relative rotation. A dose setting member or dial may be rotationally constrained via a splined interface to the dial gear, at least during dose setting and dose correction. In the at rest condition, the dial gear splines are engaged with the dial.

As an alternative, the coupling member may comprise two or more component parts, e.g. a cam ring and a dial gear. Preferably, the cam ring is rotationally constrained to the dial gear, e.g. by splines, and has a one-way ratchet interface with the dose setting member or dial. Thus, during dose setting a rotation in a first (e.g. CW) direction is transmitted from the dose setting member via the cam ring to the dial gear, which is allowed to rotate relative to the drive gear. During dose correction (CCW rotation), the one-way ratchet interface between the cam ring and the dose setting member causes axial displacement of the dial gear. Preferably, this axial displacement is used to disengage the ratchet between the drive gear and the dial gear, thus allowing the dial gear to rotate under the action of the drive spring, for example for one dose increment. In this alternative embodiment the dial gear to drive gear detent and clutch interface maximizes the security of the interface by increasing the feature size.

The device may comprise a dose setting mechanism with several interfaces. This mechanism preferably comprises the dose setting member which is rotatable relative to the housing in a first direction for dose setting and in an opposite second direction for dose correcting, a first set of ratchet teeth forming a one-way-ratchet interface provided between a drive member and a coupling member allowing rotation of the coupling member relative to the drive member in the first direction and preventing relative rotation in the opposite second direction, a cam ring which is rotationally constrained to the coupling member and axially displaceable to the coupling member, and which is in axial contact with the drive member, a second set of ratchet teeth forming a ramped interface between the dose setting member and the cam ring preventing relative rotation of the dose setting member and the cam ring in the first direction and allowing rotation of the dose setting member relative to the cam ring in the opposite second direction, wherein the rotation of the dose setting member relative to the cam ring in the opposite second direction causes an axial displacement of the cam ring relative to the dose setting member, and a drive spring biasing the coupling member in the second direction.

If the height of the first set of teeth is smaller than the height of the second set of teeth and the spacing of the first set of teeth is smaller than the spacing of the second set of teeth, a stepwise dose correction caused by the drive spring and rotation of the dose setting member may occur. For example, rotation of the dose setting member in the second direction is not transmitted to the cam ring due to the saw teeth profile. As the drive gear is held unrotatably within the chassis and is rotationally coupled via the coupling member (dial gear) to the cam ring, relative rotation occurs between dose setting member and cam ring. Due to the ramped tooth profile of the interface between cam ring and dose setting member, this causes an axial displacement of the cam ring, which acts on the drive gear, thus disengaging the interface between the drive gear and the coupling member. Now the coupling member is free to rotate together with the cam ring under the bias of the drive spring, which reduces (corrects) the set dose. As the cam ring rotates together with the coupling member, its ramped teeth slide back on the ramped teeth of the dose setting member to the fully engaged previous position, which allows the cam ring to shift back axially which re-engages the interface between the drive gear and the coupling member. In other words, the rotational movement allowed is only the spacing of two adjacent teeth of the drive gear to coupling member interface, which is typically one single dose increment (1 IU). This process may be repeated until the desired (reduced) dose is set.

According to a further aspect of the present disclosure, a spring driven drug delivery device has the mechanism axis about which the component parts rotate orientated perpendicular to the cartridge axis. This results in a compact spring driven device. For example, a drug delivery device may comprise a housing having a longitudinal axis defined by a compartment for receiving the cartridge, and a dose setting and drive mechanism for driving an, e.g. toothed, piston rod with component parts rotating about a second axis during dose setting and/or dose dispensing, wherein the second axis is perpendicular to the longitudinal axis of the housing. Preferably, the dose setting and drive mechanism further comprises a drive spring which exerts a force or torque for driving the piston rod during dose dispensing. In a preferred embodiment, the dose setting and drive mechanism comprises at least a dose setting element, e.g. a dial member, a dial gear and/or a number wheel, and a drive element, e.g. a drive gear, which are both rotatable about the second axis.

The cartridge of the drug delivery device typically contains a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 (SEQ ID NO: 1).

Exendin-4 derivatives are for example selected from the following list of compounds:

(SEQ ID NO: 2)
H-(Lys)4-des Pro36, des Pro37 Exendin-4(1-39)-NH2, (SEQ ID NO: 3)
H-(Lys)5-des Pro36, des Pro37 Exendin-4(1-39)-NH2, (SEQ ID NO: 4)
des Pro36 Exendin-4(1-39), (SEQ ID NO: 5)
des Pro36 [Asp28] Exendin-4(1-39), (SEQ ID NO: 6)
des Pro36 [IsoAsp28] Exendin-4(1-39), (SEQ ID NO: 7)
des Pro36 [Met(O)14, Asp28] Exendin-4(1-39), (SEQ ID NO: 8)
des Pro36 [Met(O)14, IsoAsp28] Exendin-4(1-39), (SEQ ID NO: 9)
des Pro36 [Trp(O2)25, Asp28] Exendin-4(1-39), (SEQ ID NO: 10)
des Pro36 [Trp(O2)25, IsoAsp28] Exendin-4(1-39), (SEQ ID NO: 11)
des Pro36 [Met(O)14 Trp(O2)25, Asp28] Exendin-4(1-39), (SEQ ID NO: 12)
des Pro36 [Met(O)14 Trp(O2)25, IsoAsp28] Exendin-4(1-39);
or (SEQ ID NO: 5)
des Pro36 [Asp28] Exendin-4(1-39), (SEQ ID NO: 6)
des Pro36 [IsoAsp28] Exendin-4(1-39), (SEQ ID NO: 7)
des Pro36 [Met(O)14, Asp28] Exendin-4(1-39),

```
                                            (SEQ ID NO: 8)
des Pro36 [Met(O)14, IsoAsp28] Exendin-4(1-39), (SEQ ID NO: 9)
des Pro36 [Trp(O2)25, Asp28] Exendin-4(1-39), (SEQ ID NO: 10)
des Pro36 [Trp(O2)25, IsoAsp28] Exendin-4(1-39), (SEQ ID NO: 11)
des Pro36 [Met(O)14 Trp(O2)25, Asp28] Exendin-4
(1-39), (SEQ ID NO: 12)
des Pro36 [Met(O)14 Trp(O2)25, IsoAsp28] Exendin-
4(1-39),
``` wherein the group -Lys6-NH2 may be bound to the C-terminus of the Exendin-4 derivative;

or an Exendin-4 derivative of the sequence

```
                                            (SEQ ID NO: 13)
des Pro36 Exendin-4(1-39)-Lys6-NH2 (AVE0010), (SEQ ID NO: 14)
H-(Lys)6-des Pro36 [Asp28] Exendin-4(1-39)-Lys6-
NH2, (SEQ ID NO: 15)
des Asp28 Pro36, Pro37, Pro38Exendin-4(1-39)-NH2, (SEQ ID NO: 16)
H-(Lys)6-des Pro36, Pro38 [Asp28] Exendin-4(1-39)-
NH2, (SEQ ID NO: 17)
H-Asn-(Glu)5des Pro36, Pro37, Pro38 [Asp28]
Exendin-4(1-39)-NH2, (SEQ ID NO: 18)
des Pro36, Pro37, Pro38 [Asp28] Exendin-4(1-39)-
(Lys)6-NH2, (SEQ ID NO: 19)
H-(Lys)6-des Pro36, Pro37, Pro38 [Asp28] Exendin-
4(1-39)-(Lys)6-NH2, (SEQ ID NO: 20)
H-Asn-(Glu)5-des Pro36, Pro37, Pro38 [Asp28]
Exendin-4(1-39)-(Lys)6-NH2, (SEQ ID NO: 21)
H-(Lys)6-des Pro36 [Trp(O2)25, Asp28] Exendin-4
(1-39)-Lys6-NH2, (SEQ ID NO: 22)
H-des Asp28 Pro36, Pro37, Pro38 [Trp(O2)25]
Exendin-4(1-39)-NH2, (SEQ ID NO: 23)
H-(Lys)6-des Pro36, Pro37, Pro38 [Trp(O2)25,
Asp28] Exendin-4(1-39)-NH2, (SEQ ID NO: 24)
H-Asn-(Glu)5-des Pro36, Pro37, Pro38 [Trp(O2)25,
Asp28] Exendin-4(1-39)-NH2, (SEQ ID NO: 25)
des Pro36, Pro37, Pro38 [Trp(O2)25, Asp28]
Exendin-4(1-39)-(Lys)6-NH2, (SEQ ID NO: 26)
H-(Lys)6-des Pro36, Pro37, Pro38 [Trp(O2)25,
Asp28] Exendin-4(1-39)-(Lys)6-NH2, (SEQ ID NO: 27)
H-Asn-(Glu)5-des Pro36, Pro37, Pro38 [Trp(O2)25,
Asp28] Exendin-4(1-39)-(Lys)6-NH2, (SEQ ID NO: 28)
H-(Lys)6-des Pro36 [Met(O)14, Asp28] Exendin-4
(1-39)-Lys6-NH2, (SEQ ID NO: 29)
des Met(O)14 Asp28 Pro36, Pro37, Pro38 Exendin-4
(1-39)-NH2, (SEQ ID NO: 30)
H-(Lys)6-desPro36, Pro37, Pro38 [Met(O)14, Asp28]
Exendin-4(1-39)-NH2, (SEQ ID NO: 31)
H-Asn-(Glu)5-des Pro36, Pro37, Pro38 [Met(O)14,
Asp28] Exendin-4(1-39)-NH2, (SEQ ID NO: 32)
des Pro36, Pro37, Pro38 [Met(O)14, Asp28] Exendin-
4(1-39)-(Lys)6-NH2, (SEQ ID NO: 33)
H-(Lys)6-des Pro36, Pro37, Pro38 [Met(O)14, Asp28]
Exendin-4(1-39)-(Lys)6-NH2, (SEQ ID NO: 34)
H-Asn-(Glu)5 des Pro36, Pro37, Pro38 [Met(O)14,
Asp28] Exendin-4(1-39)-(Lys)6-NH2, (SEQ ID NO: 35)
H-Lys6-des Pro36 [Met(O)14, Trp(O2)25, Asp28]
Exendin-4(1-39)-Lys6-NH2, (SEQ ID NO: 36)
H-des Asp28 Pro36, Pro37, Pro38 [Met(O)14, Trp(O2)
25] Exendin-4(1-39)-NH2, (SEQ ID NO: 37)
H-(Lys)6-des Pro36, Pro37, Pro38 [Met(O)14, Asp28]
Exendin-4(1-39)-NH2, (SEQ ID NO: 38)
H-Asn-(Glu)5-des Pro36, Pro37, Pro38 [Met(O)14,
Trp(O2)25, Asp28] Exendin-4(1-39)-NH2, (SEQ ID NO: 39)
des Pro36, Pro37, Pro38 [Met(O)14, Trp(O2)25,
Asp28] Exendin-4(1-39)-(Lys)6-NH2, (SEQ ID NO: 40)
H-(Lys)6-des Pro36, Pro37, Pro38 [Met(O)14,
Trp(O2)25, Asp28] Exendin-4(S1-39)-(Lys)6-NH2, (SEQ ID NO: 41)
H-Asn-(Glu)5-des Pro36, Pro37, Pro38 [Met(O)14,
Trp(O2)25, Asp28] Exendin-4(1-39)-(Lys)6-NH2;
``` or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

The present disclosure will now be described in further detail with reference to the accompanying schematic drawings, wherein FIG. 13 shows a detail of the device of FIG. 2, FIG. 14*a* shows a detail of a ratchet of the device of FIG. 2

FIG. 14*b* shows an alternative embodiment of a ratchet,

FIG. 15 shows a detail of the ratchet of FIG. 14*b*,

FIG. 16 shows a detail of the ratchet of FIG. 14*b*,

FIG. 17 shows a detail of the ratchet of FIG. 14*b*,

DETAILED DESCRIPTION

Figure 1:
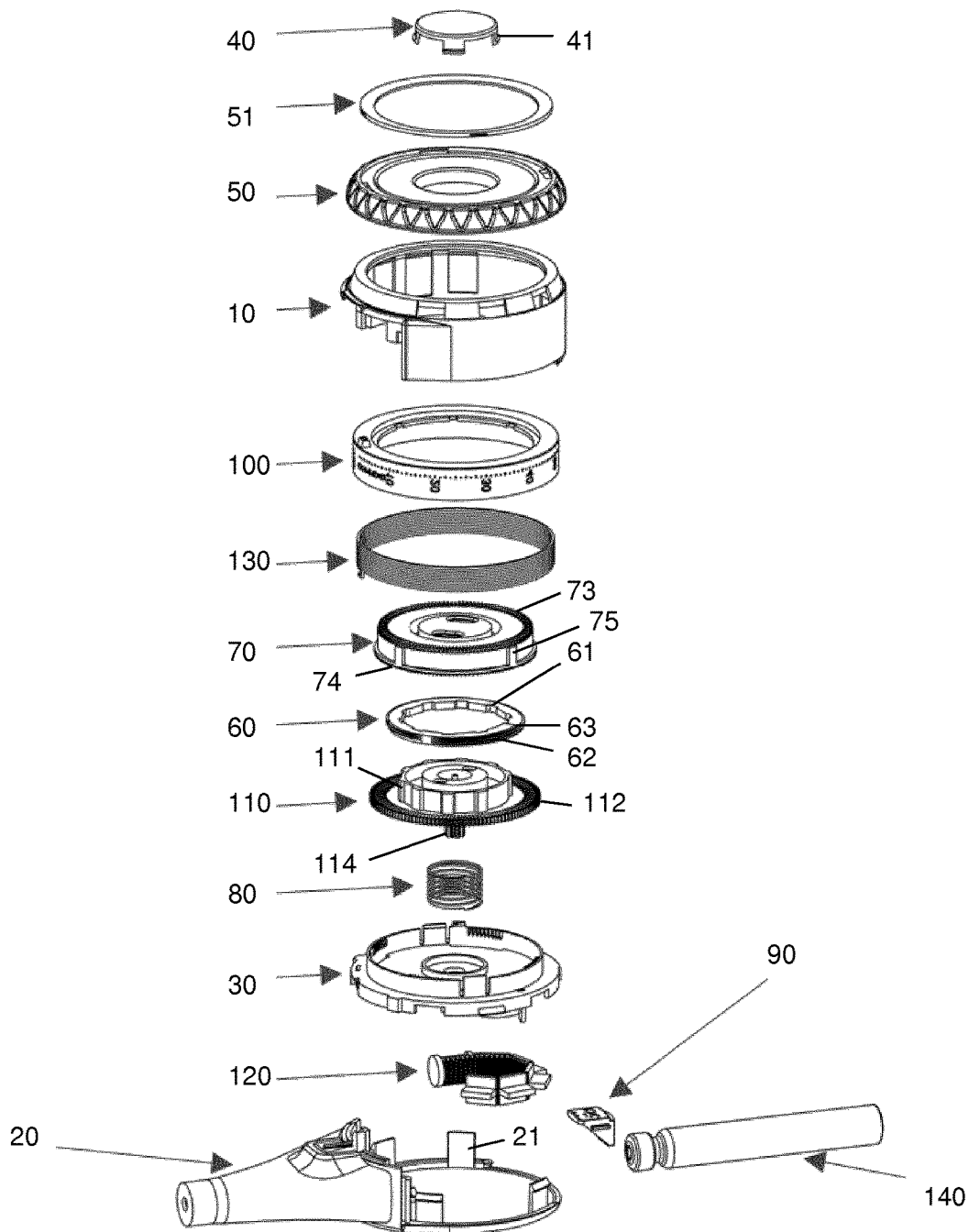
FIG. 1 shows an exploded view of an injection device comprising a drive mechanism.
Figure 2:
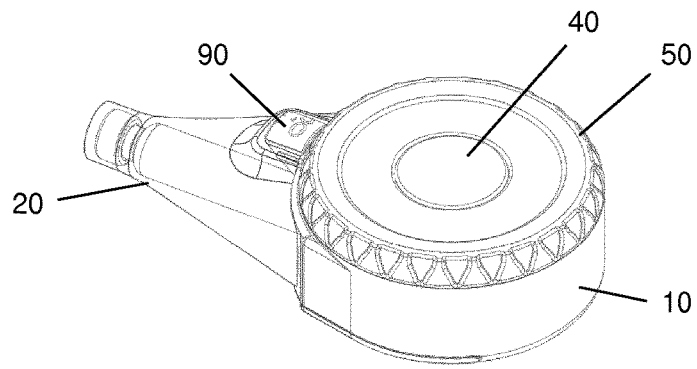
FIG. 2 shows a perspective view of the device of FIG. 1.

FIGS. 1 and 2 show views of the drug delivery device. FIG. 1 illustrates the component parts incorporated into the injection device which are a casework or body 10, a cartridge holder 20, a base element or chassis 30, a trigger or dose button 40, a dial member 50 with a dial cover 51, a last dose nut 60, a dial gear 70, a trigger spring 80, a prism 90, a number wheel 100, a drive gear 110, a flexible piston rod 120, a drive spring 130 and a medicament cartridge 140.

The casework or body 10 forms together with cartridge holder 20 the housing of the device. It is the basis for relative movements of other component parts during use of the device. Body 10 and cartridge holder 20 may be permanently attached to each other by snap hooks 21. Cartridge holder 20 has an opening into which prism 90 is inserted and permanently fixed. Further, the base element or chassis 30 is permanently attached to the body 10 and cartridge holder 20 such that these component parts behave in use as a single part. The liquid medicament cartridge 140 contains a movable bung 141 and is housed within the cartridge holder 20. Body 10 comprises a protrusion (FIG. 6) interacting with a corresponding protrusion of the number wheel 100. The upper right side (in FIG. 6) of the body protrusion forms a zero unit stop 11 and the opposite lower left side forms a maximum dose stop 12. The upper right side (in FIG. 6) of the number wheel protrusion forms a maximum dose counter stop 101 and the opposite lower left side forms a zero unit counter stop 102.

Figure 5:
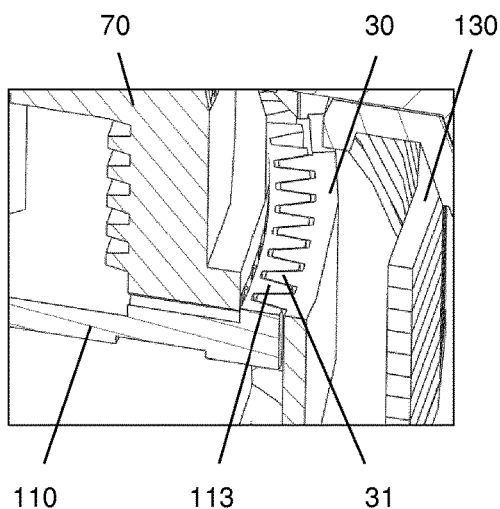
FIG. 5 shows a detail of the device of FIG. 2.
Figure 8:
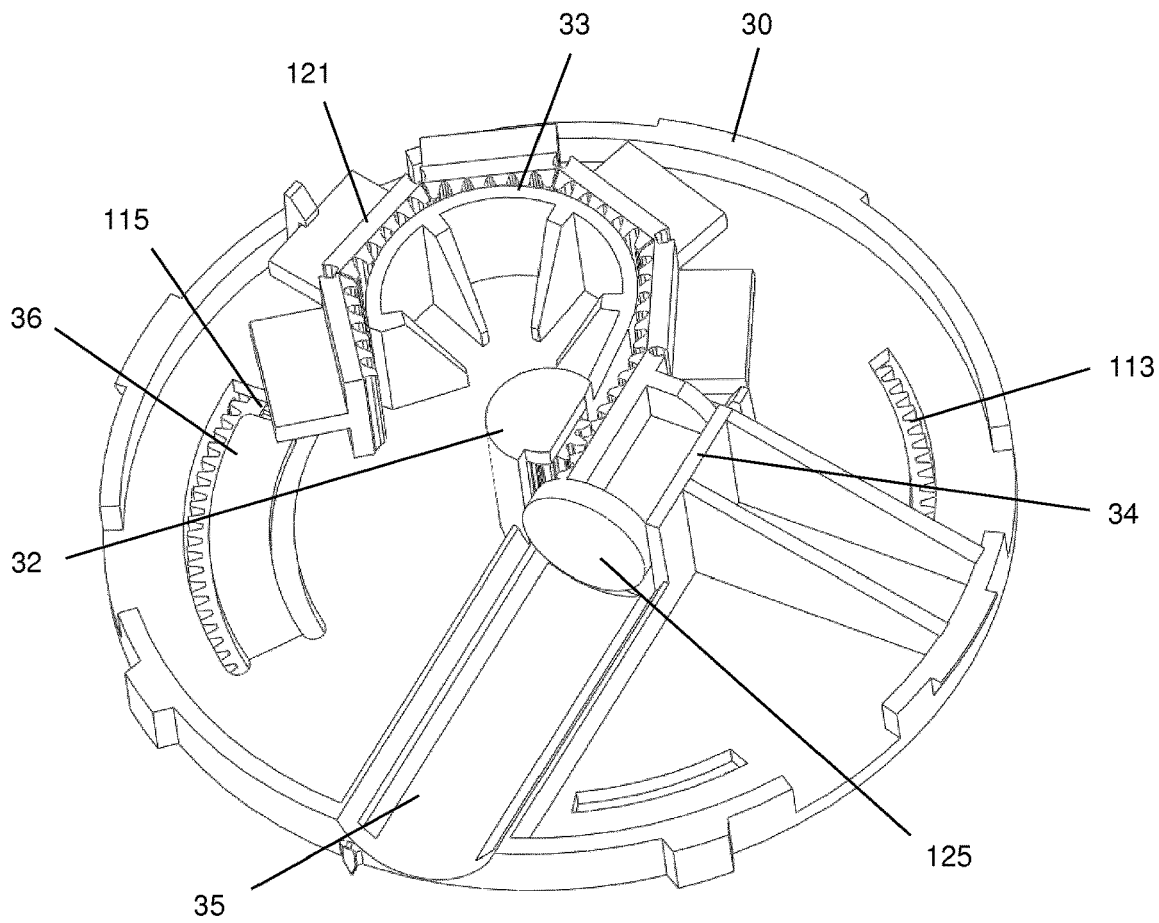
FIG. 8 shows components of the drive mechanism of the device of FIG. 2.
Figure 11:
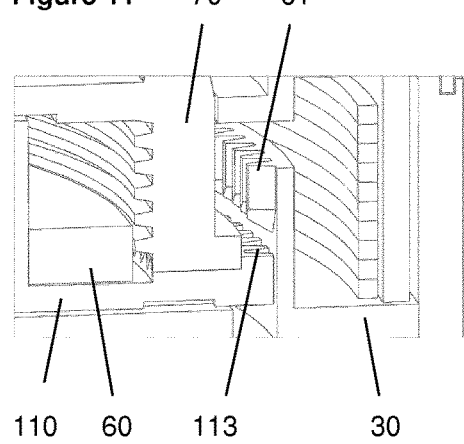
FIG. 11 shows the detail of FIG. 5 in the dose dispensing condition.

Chassis 30 is a disc-like component with a generally circular configuration. Splines 31 are provided at an inner side for releasably engaging drive gear 110 (FIGS. 5 and 11). Chassis 30 comprises a bearing 32, which may have the form of a cut open cylinder located at the center of chassis 30, for receiving a pinion of the drive gear (FIG. 8). Further, a first curved guiding section 33 a second straight guiding section 34 and a receiving section 35 for retaining the cartridge 140 are provided. A clicker arm 36 is located within the disc-shaped chassis 30 (FIGS. 8 and 13).

The trigger or dose button 40 is axially constrained between the dial 50 and dial gear 70. It may be fixed to the dial gear 70 by snap hooks 41. Dose button 40 is axially displaceable relative to the body 10 and to the dial 50.

The dial 50 is axially constrained to the body 10 via clip features (not shown in FIG. 1). It is rotationally constrained, via a splined interface, to the dial gear 70. This splined interface is disconnected when the dose button 40 is pressed. The dial 50 may have the form of a disc or ring with a serrated outer surface as indicated in FIG. 1. The dial cover 51 is rigidly fixed into the dial 50.

Figure 12:
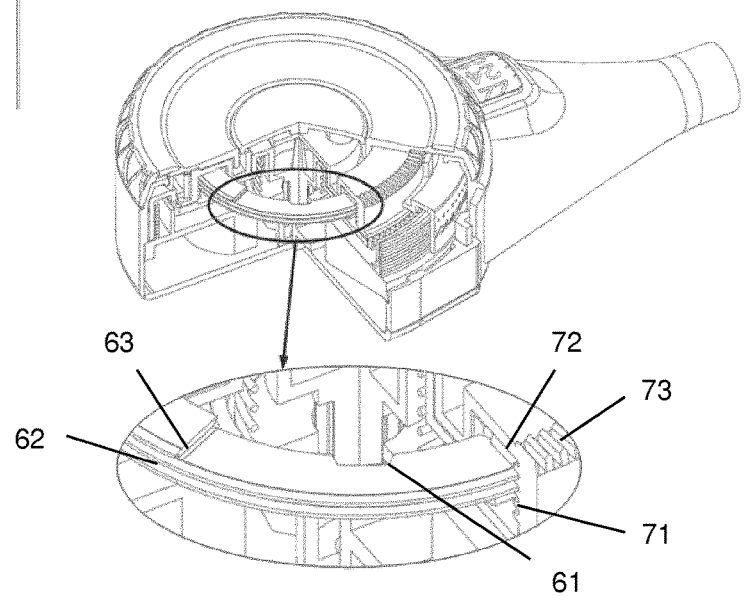
FIG. 12 shows a detail of the device of FIG. 2.

The last dose nut 60 is located between the dial gear 70 and drive gear 110. It is rotationally coupled to the drive gear 110, via a splined interface (grooves 61 and splines 111). It moves along a helical path relative to the dial gear 70, via a threaded interface (outer thread 62 and inner thread 71), when relative rotation occurs between the dial gear 70 and drive gear 110 (i.e. during dialing). A rotational end stop 63 is provided on the nut 60 for engagement with a last dose stop 72 on dial gear 70 (FIG. 12).

Figure 4:
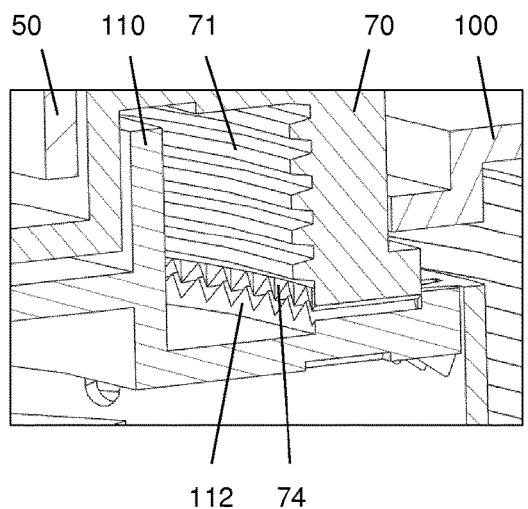
FIG. 4 shows a detail of the device of FIG. 2.

Dial gear 70 is a cup shaped member with an annular recess in its upper surface (in FIG. 1) for receiving a skirt of dial 50 and dose button 40. Dial gear 70 has an interface (inner thread 71, last dose stop 72) with the last dose nut 60. Its upper surface is provided with a ring of axially extending teeth 73 engaging corresponding spline teeth on the lower side of dial 50. The opposite lower skirt face comprises ratchet teeth 74 interacting with corresponding ratchet teeth 112 of drive gear 110 (FIG. 4). Splines 75 engage a corresponding interface of number wheel 100. Slots 76 may engage splines of a cam ring provided in an alternative embodiment. A clicker arm 77 interacts with a ramp 37 of chassis 30 at the end of dose dispensing. Cut-outs 78 may be provided to allow access to drive gear 110 during the assembly process.

The trigger spring 80 applies a force between the chassis 30 and drive gear 110 to separate them. In the "at rest" condition, this ensures that the drive gear 110 is rotationally coupled to the chassis 30 and that the spline teeth 73 of dial gear 70 are engaged with the dial 50 (FIGS. 5 and 11).

Figure 6:
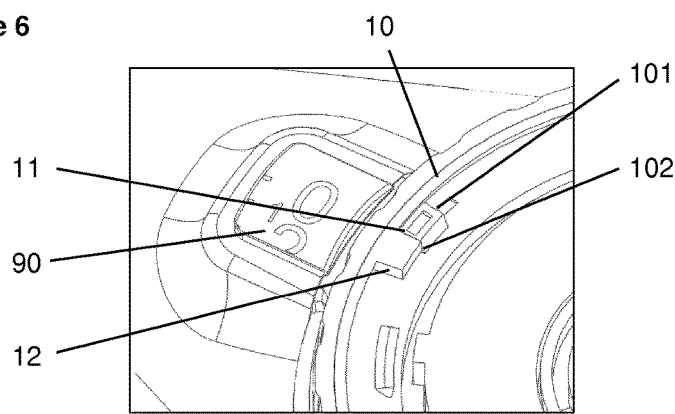
FIG. 6 shows a detail of the device of FIG. 2, FIGS. 7*a* & *b* show the piston rod of the device of FIG. 1 in a flexed position and in a straight position.

The dose set is displayed on the outer surface of the device to provide feedback to the user. In this embodiment, the prism 90 reflects the display from the number wheel 100 so that the dose is displayed on the front face of the device (FIG. 6). The prism 90 is retained within the cartridge holder 20 and body 10 once assembled. The prism 90 uses the phenomenon of "Total Internal Reflection" to achieve reflection of the number without any special treatment to the surfaces (such as metal coating). The nature of this prism is that the display is mirrored. To account for this, the printing on the number wheel 100 is reversed so the net effect provides a conventional dose number displayed. An additional function of the prism 90 is that the surfaces can be designed to also provide magnification, in addition to the primary function of reflection. Alternative prism arrangements (for example a Penta-prism) could perform the same function without mirroring the display if required.

An alternative embodiment negates the requirement for the prism 90 component and displays the dose on the side of the device. The number wheel 100 is then printed with conventional, non-mirrored, text and a small window is formed in the side of the body 10.

The number wheel 100 is axially constrained between the chassis 30 and body 10. It is rotationally coupled to the dial gear 70, via a splined interface (splines 75), that permits relative axial movement between the dial gear 70 and number wheel 100. The number wheel 100 is free to rotate, relative to the body 10, between two fixed, rotational stops formed by abutments on the number wheel 100 and body 10. A sequence of numbers, markings or symbols is provided on the outer circumference of the number wheel 100.

The drive gear 110 is axially constrained between the chassis 30 and dial gear 70 and biased away from the chassis 30 by the trigger spring 80. It is rotationally coupled to the dial gear 70 via a detent and clutch interface (FIG. 4), which occurs on an axial abutment. The detent and clutch interface 74, 112 provides a detented position between the dial gear 70 and drive gear 110 corresponding to each dose unit, and engages different ramped tooth angles during CW (clockwise) and CCW (counter-clockwise) relative rotation. The drive gear 110 is rotationally coupled to the chassis 30, via a splined interface 31, 113 (FIG. 5). When the dose button 40 is pressed, this spline interface 31, 113 is disengaged and ratchet features 115 interact with clicker arm 36 (FIG. 13), providing audible feedback during dose delivery. Further, the drive gear 110 comprises a pinion 114 engaging the flexible piston rod 120. Location features 116, e.g. in the form of openings, may be provided for engagement with a tool during the assembly process.

Figure 7A:
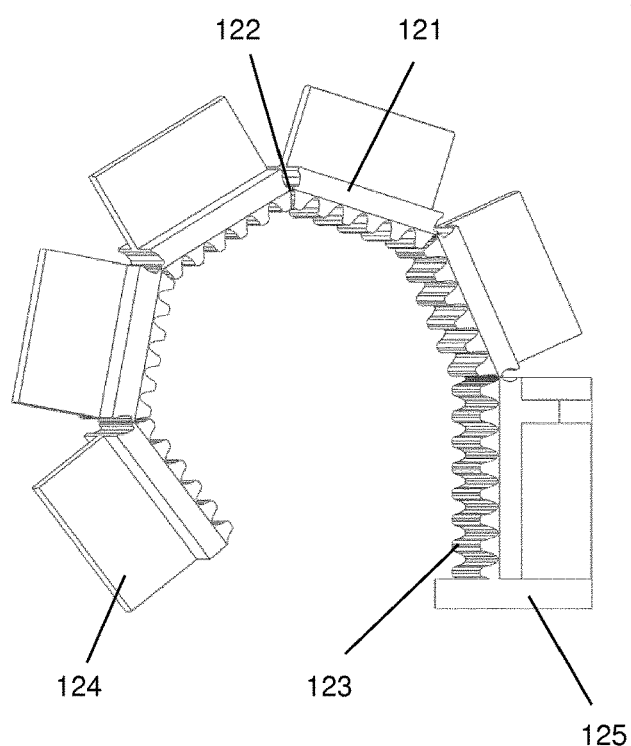
Figure 7B:
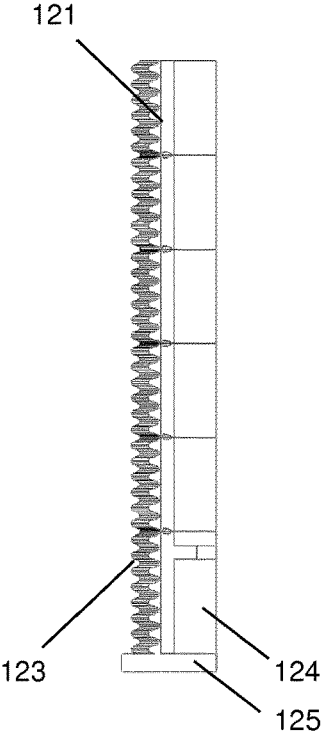

The flexible piston rod 120 is located within the chassis 30 and engages, via a rack and pinion interface, the drive gear 110 so that CCW rotation of the drive gear 110 advances the piston rod 120. The distal end of the piston rod 120 acts on the bung 141 within the liquid medicament cartridge 140. As shown in FIGS. 7a and 7b, the piston rod 120 is a single component with discrete rigid rod pieces or segments 121 connected together by thin sections of material which form flexible hinges 122. The end faces of the segments 121 are planar and, when the piston rod 120 is straightened (FIG. 7b) the adjacent segment faces abut each other, allowing the component to withstand a compressive load. Segments 121 are shaped as a flat plate provided with rack teeth 123 on one side and a flange 124 on the opposite side. The segment facing towards the cartridge (lower segment in FIG. 7b) comprises a pressure foot 125 for contacting the cartridge bung. The piston rod 120 is restrained within the chassis 30 to maintain the flexed state and prevent the rack gear teeth from disengaging from the drive gear 110 (FIG. 8). As the piston rod 120 is advanced, via the rack 123 and pinion 114 engagement with the drive gear 110, the trailing segments 121 of piston rod 120 are drawn into engagement with the drive gear pinion 114. The subsequent segments 121 drive the preceding segments, loading them in compression, and apply a force to the bung. As the piston rod 120 advances, the first segment moves out of the support 34 provided by the chassis 30. Without additional support it is likely that the piston rod 120 would buckle under this compressive loading. The additional support to prevent buckling is created by the inner side wall of the cartridge 140 providing constraint to the outer surfaces of the piston rod 120.

Figure 3:
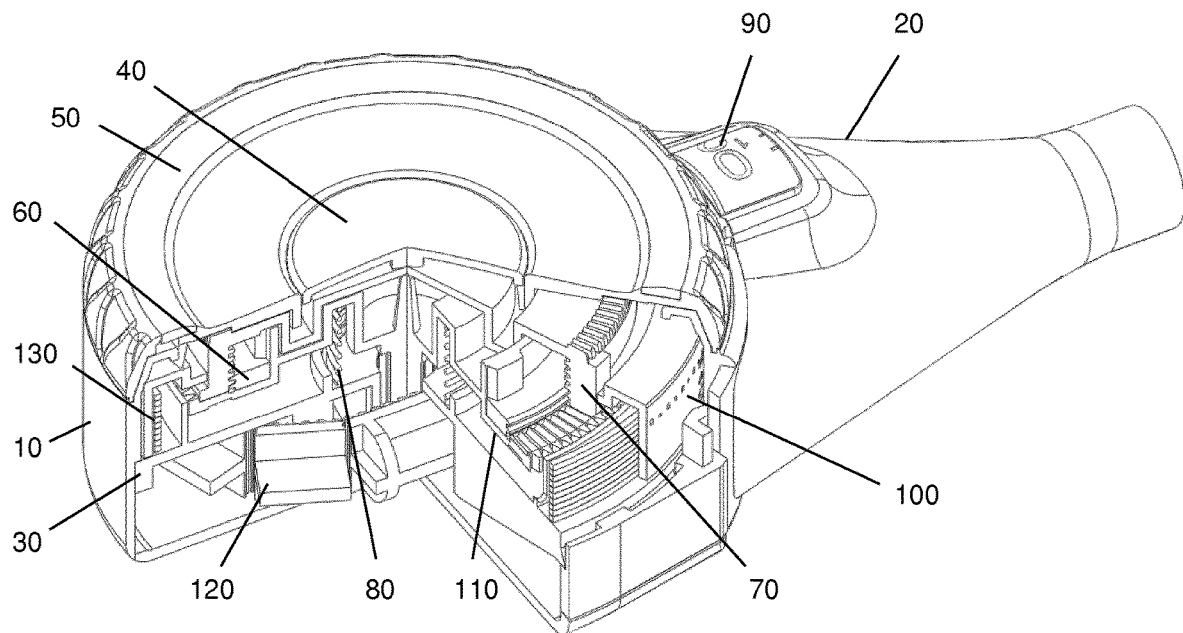
FIG. 3 shows cut-away view of the device of FIG. 2.

The drive spring 130 is attached at one end to the chassis 30 and at the other end to the number wheel 100. The drive spring 130 is pre-wound upon assembly, such that it applies a torque to the number wheel 100 when the mechanism is at zero units dialed. The action of rotating the dial 50, to set a dose, rotates the dial gear 70 and number wheel 100 relative to the chassis 30, and (further) winds up the spring. As shown in FIG. 3, drive spring 130 is located radially interposed between chassis 30 and number wheel 100. The mechanism contains the helical drive spring 130 to store energy, which is charged during setting of the dose, by the action of the user rotating the dial 50. The spring energy is stored until the mechanism is triggered for dispense at which point the energy stored is used to deliver the medicament from the cartridge to the user.

The drug delivery device can be operated to deliver a number of user variable doses of medicament from the cartridge 140, via a needle (not shown). The device is disposable and is delivered to the user in a fully assembled condition ready for use. The mechanism provides separate user interfaces for setting and delivery of a dose. In short, a dose is set by rotating dial 50 located on the face of the device. Delivery of a dose is initiated by pressing dose button 40, positioned in the center of the dial 50, and dose delivery will continue while the dose button 40 remains depressed, until the complete set dose has been delivered. The mechanism provides audible, visual and tactile feedback both on the setting and delivery of each dose. Any dose size can be selected between zero and a pre-defined maximum, in increments to suit the medicament and user profile. The mechanism permits cancelling of a dose without any medicament being dispensed by rotation of the dial 50 in the opposing direction to when selecting a dose.

The force required to actuate the dose button 40 and the distance which it has to move are small, providing a significant ergonomic advantage, particularly for those users with impaired dexterity. The mechanism requires consistent user input forces to set a dose and initiate the delivery of a dose, which are insensitive to variations in the force required to displace the bung 141 within the cartridge 140. The dial 50 is disengaged during dose delivery so that it does not rotate which improves handling of the device during use. The device has relatively low part count, very compact size and is particularly attractive for cost sensitive device applications.

In the following use and function of the device will be described in more detail.

With the device in the at rest condition, dose marking '0' on the number wheel 100 is visible through the prism 90 in the Body (FIGS. 2 and 3). The drive spring 130, which has a number of pre-wound turns applied to it during assembly of the device, applies a torque to the dial gear 70 via the spline interface with the number wheel 100. The dial gear 70 is prevented from rotating, under the action of this torque, by its detent and clutch interface 74, 112 with the drive gear 110. The drive gear 110 is prevented from rotating by the interlock provided by the engagement of splined teeth 113, 31 on the drive gear 110 and chassis 30.

The user selects a variable dose of liquid medicament by rotating the dial 50 CW, which generates an identical rotation in the dial gear 70. Rotation of the dial gear 70 causes rotation of the number wheel 100, which in turn causes wind up of the drive spring 130, increasing the energy stored within it. The drive gear 110 is still prevented from rotating, due to the engagement of its splined teeth 113 with the chassis 30. Relative rotation must therefore occur between the dial gear 70 and drive gear 110, via the detent and clutch interface 74, 112.

The user torque required to rotate the dial 50 is a sum of the torque required to wind up the drive spring 130, and the torque required to overhaul the ratchet feature 74, 112. The trigger spring 80 acts to provide an axial force to engage the ratchet feature 74, 112 and to bias the components (drive gear 110, dial gear 70 and dose button 40) away from the chassis 30 and towards the dial 50. The axial load acts to maintain the ratchet teeth 74, 112 engagement of the dial gear 70 and drive gear 110. The torque required to overhaul the ratchet 74, 112 is resultant from the axial load applied by the trigger spring 80, the CW ramp angle of the ratchet 74, 112, the friction coefficient between the mating surfaces and the mean radius of the ratchet features.

As the user rotates the dial 50 sufficiently to increment the mechanism by 1 unit, the dial gear 70 rotates relative to the drive gear 110 by one ratchet tooth 74, 112. At this point the ratchet teeth re-engage into the next detented position. An audible click is generated by the ratchet re-engagement, and tactile feedback is given by the change in torque input required.

Relative rotation of the dial gear 70 and the drive gear 110 causes the last dose nut 60 to travel axially, via the threaded engagement with the dial gear 70, towards the last dose abutment 72 on the dial gear 70 (FIG. 12).

The selected dose is displayed through the body 10 via the number wheel 100 and prism 90 as described previously. Irrespective of whether the dial 50 is rotated CW or CCW, the dose displayed will always indicate the dose to be dispensed. In addition, the dose display also decrements as the dose is dispensed and thus displays the dose remaining to be dispensed. CW rotation of the dial gear 70 rotates the number wheel 100 away from the zero unit stop 11 on the body 10 (FIG. 6) and towards the maximum unit stop 12. The dial 50 can be rotated by the user in both CW and CCW directions when the number wheel 100 is not in contact with the zero dose abutments 11,102 or the maximum dose stop abutments 12, 101. The zero unit abutment prevents CCW rotation of the dial 50 below the zero unit position. The maximum dose abutment prevents setting of a dose greater than the mechanism maximum.

With no user torque applied to the dial 50, the dial gear 70 is now prevented from rotating under the action of the torque applied by the drive spring 130, solely by the ratchet engagement 74, 112 between the dial gear 70 and the drive gear 110. The torque necessary to overhaul the ratchet in the CCW direction is resultant from the axial load applied by the trigger spring 80, the CCW ramp angle of the ratchet 74, 112, the friction coefficient between the mating surfaces and the mean radius of the ratchet features. The torque necessary to overhaul the ratchet must be greater than the torque applied to the number wheel 100 (and hence dial gear 70) by the drive spring 130. The ratchet ramp angle is therefore increased in the CCW direction to ensure this is the case.

The user may now choose to increase the selected dose by continuing to rotate the dial 50 in the CW direction. The process of overhauling the detent and clutch interface 74, 112 between the dial gear 70 and drive gear 110 is repeated for each dose unit. Additional energy is stored within the drive spring 130 for each dose unit and audible and tactile feedback is provided for each unit dialled by the re-engagement of the teeth 74, 112. The torque required to rotate the dial 50 increases as the torque required to wind up the drive spring 130 increases. The torque required to overhaul the ratchet in the CCW direction must therefore be greater than the torque applied to the dial gear 70 by the drive spring 130 when the maximum dose has been reached.

If the user continues to increase the selected dose until the maximum dose limit 12, 101 is reached, the number wheel 100 engages with its maximum dose abutment on the body 10, which prevents further rotation of the number wheel 100, dial gear 70 and dial 50. At this point the maximum dose marking on the number wheel 100 is aligned to the prism 90 and shown on the front of the device.

Depending on how many units have already been delivered by the mechanism, during selection of a dose, end stop 63 of the last dose nut 60 may contact its last dose abutment 72 with the dial gear 70 (FIG. 12). The abutment 72 prevents further relative rotation of the dial gear 70 and the drive gear 110, and therefore limits the dose that can be selected. The position of the last dose nut 60 is determined by the total number of relative rotations between the dial gear 70 and drive gear 110, which have occurred each time the user sets a dose.

With the mechanism in a state in which a dose has been selected, the user is able to deselect any number of units from this dose. Deselecting a dose is achieved by the user rotating the dial 50 CCW. The torque applied to the dial 50 by the user is sufficient, when combined with the torque applied by the drive spring 130, to overhaul the ratchet 74, 112 between the dial gear 70 and drive gear 110 in the CCW direction. When the ratchet is overhauled, CCW rotation occurs in the number wheel 100 (via the dial gear 70), which returns the number wheel 100 towards the zero dose position, and unwinds the drive spring 130. The relative rotation between the dial gear 70 and drive gear 110 causes the last dose nut 60 to return axially, away from the last dose abutment.

Figure 18A:
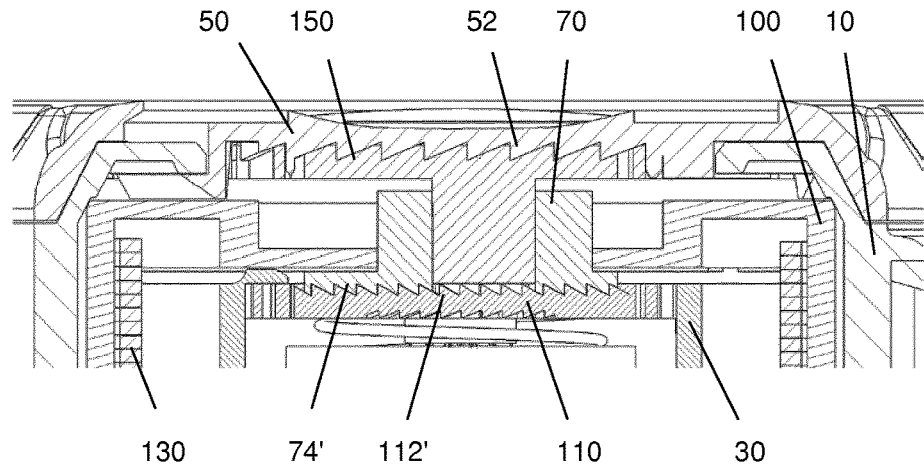
FIGS. 18*a* to 18*d* show a sequence of movements in the ratchet of FIG. 14*b*.
Figure 18B:
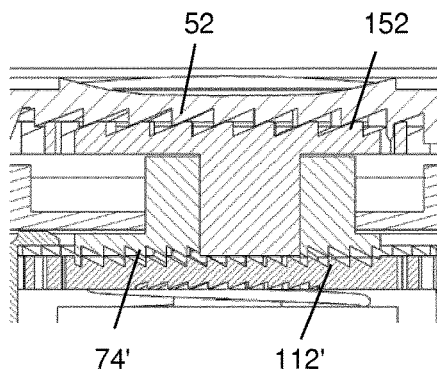

An alternative embodiment of the dial gear 70 to drive gear 110 interface depicted in FIG. 18*a* maximizes the security of the interface by increasing the feature size. The ratchet teeth profile is altered such that the ratchet teeth 74', 112' are saw-tooth shaped (FIG. 18*b*). The effect of this is that the engagement height is increased but it is no longer possible to overhaul the interface when rotating the dial 50 CCW. In order to allow decrement of a set dose the dial gear 70 and dial 50 are modified and an additional component, the cam ring 150, is required which is depicted in FIGS. 16 and 18*a* to 18*d*. FIG. 15 shows the underside of dial 50 alternative spline features to engage with cam ring 150 and FIG. 17 shows the design of dial gear 70 of the alternative embodiment.

Cam ring 150 comprises four splines 151 which engage with slots 76 dial gear 70. On its upper side facing towards the dial 50, the cam ring 150 is provided with ramp-like saw teeth 152 engaging corresponding ramp-like saw teeth 52 of the dial. In addition, straight spline features 53 and 153 are provided on the dial 50 and the cam ring 150 (FIGS. 15 and 16).

During dose set (CW dial rotation) the vertical abutments of ramp-like saw teeth 52 of dial 50 engage with vertical abutments of ramp-like saw teeth 152 of the cam ring 150 to directly transmit torque to the dial gear 70 via the spline engagement (splines 151 and slots 76) between the cam ring 150 and dial gear 70. Rotation of the dial gear 70 causes wind up of the drive spring 130, increasing the energy stored within it. The drive gear 110 is still prevented from rotating, due to the engagement of its splined teeth 113 with the chassis 30. Relative rotation must therefore occur between the dial gear 70 and drive gear 110, via the detent and clutch interface 74', 112'. The at rest position is shown in FIG. 18*a*.

When the dial 50 is rotated CCW the dial gear 70 and cam ring 150 are not carried by it due to the profile of the detent and clutch interface (74', 112') between the dial gear 70 and drive gear 110 (which is rotationally coupled to the chassis 30 throughout the dose select or deselect action). CCW rotation of the dial 50, therefore, results in relative rotation between the cam ring 150 and dial 50. The ramp features of saw teeth 52, 152 between dial 50 and cam ring 150 cause the cam ring 150 to displace axially as a result of the relative rotation (FIG. 18*b*). The cam ring 150 applies an axial force to the drive gear 110, displacing it against the trigger spring 80 force, separating the drive gear 110 and dial gear 70 and disengaging the detent and clutch interface 74' and 112'.

When the dial 50 has rotated sufficiently to disengage detent and clutch interface 74', 112', splines 53 on the dial 50 contact splines 153 on the cam ring 150 and prevent further relative rotation between the dial 50 and cam ring 150. Clearance between the splines 53, 153 allows enough relative rotation of the dial 50 and cam ring 150 to disengage detent and clutch interface 74', 112', but not enough for the saw-teeth 52, 152 to override each other and cause the dial 50 to become de-synchronised with the cam ring 150 and dial gear 70.

Figure 18C:
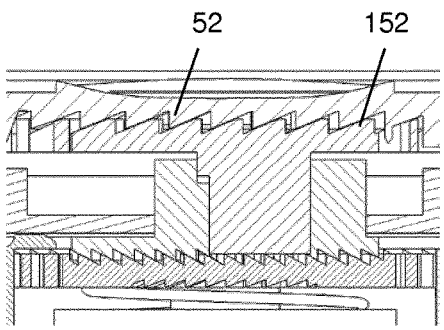

Detent and clutch interface (74', 112') reacts the drive spring 130 torque, applied to the dial gear 70 via the number wheel 100. When the detent and clutch interface is disengaged, the drive spring 130 torque rotates the dial gear 70 CCW by one unit increment via the number wheel 100 (FIG. 18*c*). Rotation of the dial gear 70 may also be assisted by the user torque applied to the dial 50 and transferred to the cam ring 150 via splines 53, 153 and further to the dial gear 70 via splines 76, 151.

Figure 18D:
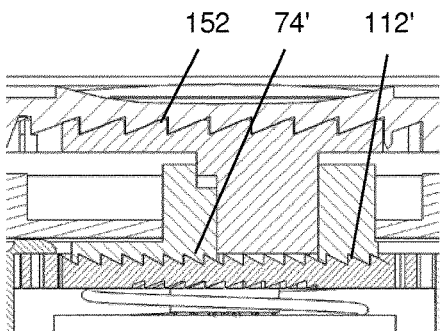

The cam ring 150 is then driven rotationally by the dial gear 70, relative to the dial 50, returning along the helical path and to its original axial position. The trigger spring 80 returns the drive gear 110 axially and re-engages the detent and clutch interface 74' and 112' between dial gear 70 and drive gear 110 (FIG. 18*d*). At this stage the dial 50 may be rotated in either a CW direction to select a higher dose or a CCW to further reduce the dose set.

Figure 9:
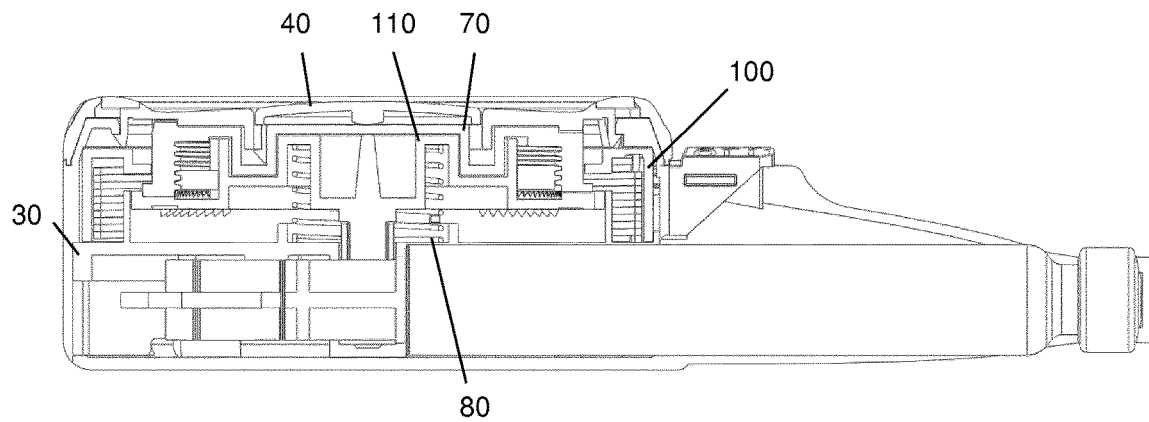
FIG. 9 shows a partial sectional view of a detail of the device of FIG. 2 in the dose setting condition.
Figure 10:
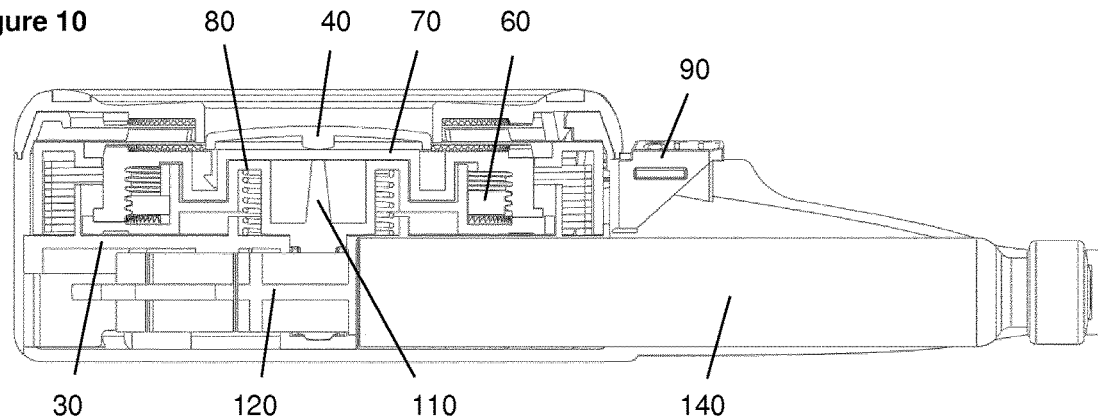
FIG. 10 shows a partial sectional view of a detail of the device of FIG. 2 in the dose dispensing condition.

With any of the above mentioned alternative mechanisms in a state in which a dose has been selected, the user is able to activate the mechanism to commence delivery of a dose. Delivery of a dose is initiated by the user depressing the dose button 40 in the center of the dial 50. FIG. 9 shows the device with dose button 40 released as during dose setting and dose correction, while FIG. 10 shows the device with dose button 40 depressed for dose dispensing.

When the dose button 40 is depressed, it moves axially, acting on the dial gear 70, which in turn acts on the drive gear 110. The dial gear 70 disengages its spline teeth 73 from the dial 50 and then the drive gear 110 disengages its spline teeth 113 from the corresponding teeth 31 of the chassis 30 (FIG. 11). When the splined interface 31, 113 between the chassis 30 and the drive gear 110 disengage, the interface which prevents rotation of the drive gear 110 during selection of a dose is removed. Thus, the order of disengagement is important to prevent unintended discharging of the drive spring 130.

The torque applied to the dial gear 70, via the number wheel 100, from the drive spring 130 is transmitted, via the detent and clutch interface, into the drive gear 110. This torque causes rotation of the drive gear 110 and hence, due to its geared engagement with the piston rod 120, advancement of the piston rod 120. Axial displacement of the piston rod 120 forces liquid medicament to be delivered from the mechanism, as the distal end of the piston rod 120 contacts and displaces the bung 141 within the cartridge 140. The rotation of the dial gear 70 also causes the number wheel 100 to rotate CCW, towards the zero dose abutment and decrementing the dose displayed.

The clicker arm 36 is a compliant cantilever beam integrated into the chassis 30, which interfaces axially with ratchet features 115 on the drive gear 110. The ratchet teeth spacing corresponds to the drive gear 110 rotation required to deliver a single dose unit. During dispense, as the drive gear 110 rotates, the ratchet features 115 engage with the clicker arm 36 to produce an audible click with each dose unit delivered (FIG. 13). The torque required to overhaul the clicker arm 36 is resultant from the profile of ratchet teeth 115, the stiffness of the cantilever beam and the nominal interference between clicker arm 36 and ratchet 115. The clicker arm interface is designed such that the torque required to overhaul is significantly less than the torque provided by the drive spring 130.

Delivery of a dose continues via the mechanical interactions described above while the user continues to depress the dose button 40. If the user releases the dose button 40, the trigger spring 80 returns the dose button 40 to its at rest position via the drive gear 110 and dial gear 70, the drive gear 110 becomes rotationally constrained and delivery of a dose is halted.

With the dose button 40 depressed, delivery of a dose continues until the number wheel 100 reaches the zero dose abutment 102 with the body 10. The torque applied to the number wheel 100 by the drive spring 130 is reacted by the abutment of the number wheel 100 to the body 10 and the number wheel 100, dial gear 70 and drive gear 110 are prevented from rotating further. During delivery of a dose, the drive gear 110 and dial gear 70 rotate together, so that no relative motion in the last dose nut 60 occurs. The last dose nut 60 therefore travels towards its abutment on the dial gear 70 during dialing only.

Once the delivery of a dose is stopped, by the number wheel 100 returning to the zero dose abutment 11, the user may release the dose button 40, which will re-engage the chassis 30 spline teeth 31 with teeth 113 of the drive gear 110. The mechanism is now returned to the at rest condition.

Figure 19:
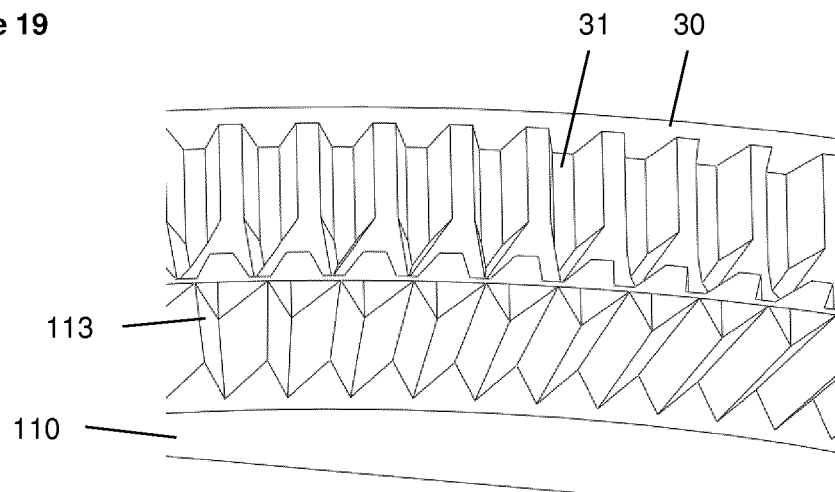
FIG. 19 shows a detail of the device of FIG. 2, FIGS. 20*a* to 20*d* show an end of dose click sequence of the device of FIG. 2, FIGS. 21*a-b* show the mechanism of FIGS. 20*a* to 20*d* in the dose setting condition and in the dose dispensing condition.

It is possible to angle either the spline teeth 113 on the drive gear 110 or the spline teeth 31 on chassis 30 so that when the dose button 40 is released the re-engagement of the spline teeth 31, 113 fractionally 'backwind' the drive gear 110 thereby removing the engagement of the number wheel 100 to the chassis 30 zero dose stop abutment (FIG. 19). This removes the effect of clearances in the mechanism (for example due to tolerances) which could otherwise lead to slight advancement of the piston rod 120 and medicament dispense when the device is dialed dialled for the subsequent dose (due to the number wheel 100 zero dose stop no longer restraining the mechanism and instead the restraint returning to the splines between the drive gear 110 and chassis 30).

Figure 21A:
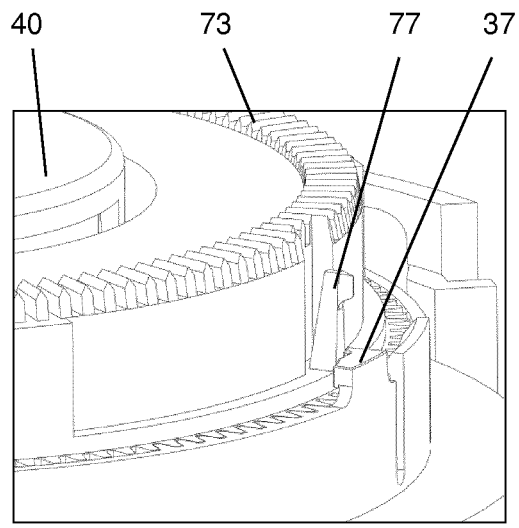
Figure 21B:
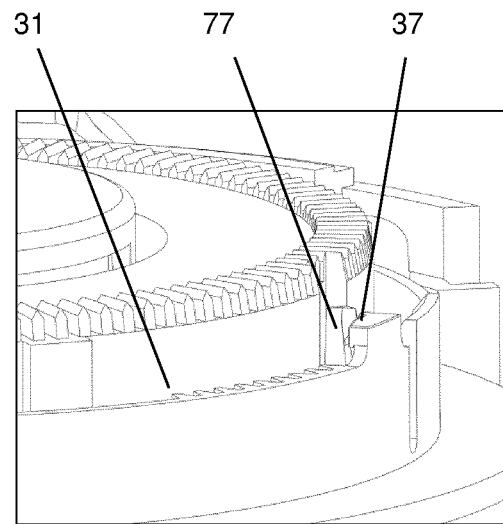

An audible click occurs at the end of dose when the mechanism reaches its zero position 11, 102. The click is created by interaction between ramp 37 of the chassis 30 and a flexible clicker arm 77 on the dial gear 70 when the dial gear 70 is in the dispensing axial position. The advantage with this design is that the click feedback only occurs during dose delivery (FIG. 21*b*), i.e. when button 40 and dial gear 70 are depressed, and not during dialing or cancelling of a dose, when clicker arm 77 and ramp 37 are axially spaced as shown in FIG. 21*a*.

Figure 20A:
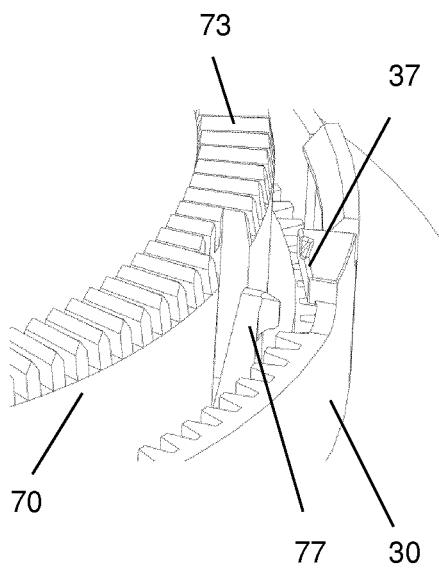
Figure 20B:
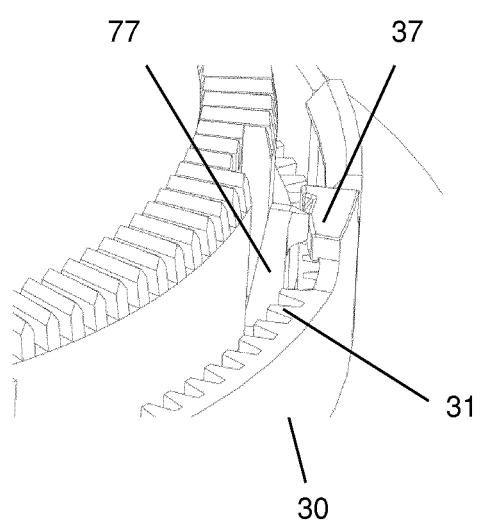
Figure 20C:
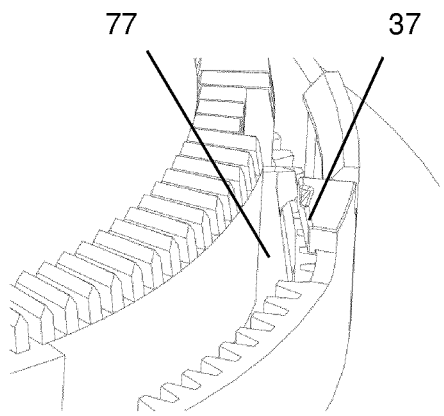
Figure 20D:
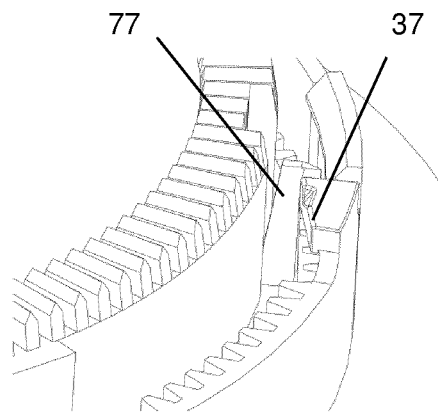

The sequence of generating the click is shown in FIGS. 20*a* to 20*d*, with FIG. 20*a* depicting the situation that e.g. 6 units are remaining and clicker arm 77 approaches ramp 37. In FIG. 20*b* there are 2 units remaining and clicker arm 77 contacts ramp 37 of chassis 30. FIG. 20*c* shows the interface just prior to the click with 0.5 units remaining. The clicker arm 77 is deflected against ramp 37. The end of dose is shown in FIG. 20*d*, when the audible click is generated as clicker arm 77 passes off ramp 37 of chassis 30.

Figure 22:
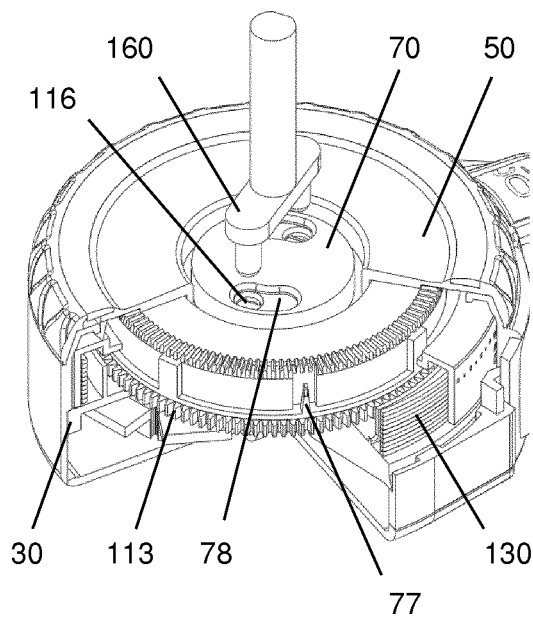
FIG. 22 shows the application of a tool during assembly of the device of FIG. 2.
Figure 23:
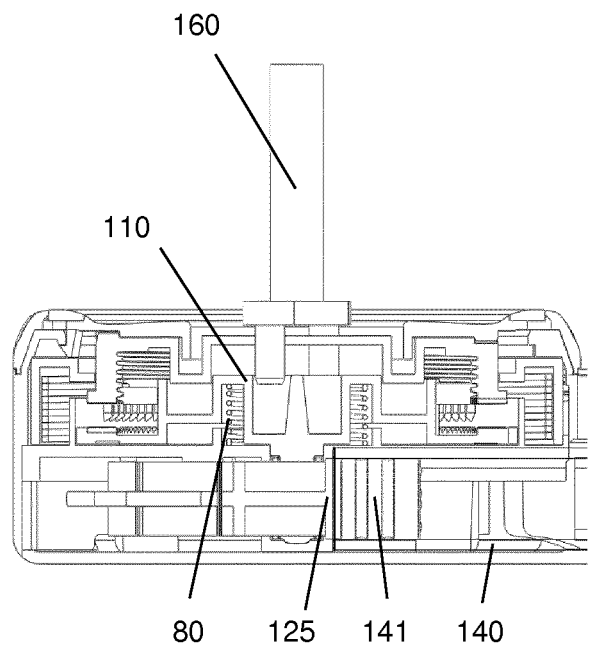
FIG. 23 shows in a sectional view the use of the tool of FIG. 22.

A further aspect of the present disclosure pertains to the facility for removing the need for a user to prime the device when first used. This involves removing the variable distance (dependent on component and cartridge tolerances) between the bung 141 of cartridge 140 and the distal face (foot 125) of the piston rod 120 during manufacture such that the piston rod 120 is in contact with the bung 141 when assembled. For this prime elimination the device is assembled completely, however omitting the dose button 40. An assembly tool 160 engages with location features 116 in the drive gear 110, through cut-outs 78 in the dial gear 70 (FIG. 22). The detent and clutch interface 74, 112 between the dial gear 70 and drive gear 110 is disengaged by axially translating the drive gear 110 towards the chassis 30, compressing the trigger spring 80 (FIG. 23). In this state of the device the drive gear 110 is rotated CCW by the assembly tool 160 until the torque required to rotate the drive gear 110 reaches a pre-determined value, corresponding to the required axial force applied to the bung 141 by the piston rod 120. The assembly tool 160 is then retracted, allowing the trigger spring 80 to return the drive gear 110 to the at rest position where it is rotationally constrained by the spline engagement to the chassis 30. Finally, the dose button 40 is fitted into the dial 50 via snap clip features 41.

As an alternative to the embodiments depicted in the Figures which comprise a prism, a window or opening may be provided in the body, for example in the cylindrical side surface, through which markings of the number wheel 100 are visible.

| Reference numerals | |
|---|---|
| 10 | body (casework) |
| 11 | minimum stop |
| 12 | maximum stop |
| 20 | cartridge holder |
| 21 | snap hook |
| 30 | chassis (base element) |
| 31 | spline teeth |
| 32 | bearing |
| 33 | first curved guiding section |
| 34 | second straight guiding section |
| 35 | receiving section |
| 36 | clicker arm |
| 37 | ramp |
| 40 | dose button |
| 41 | snap hook |
| 50 | dial (dose setting member) |
| 51 | dial cover |
| 52 | saw teeth |
| 53 | spline |
| 60 | last dose nut |
| 61 | groove |
| 62 | outer thread |
| 63 | end stop |
| 70 | dial gear (coupling element) |
| 71 | thread |
| 72 | stop |
| 73 | teeth |
| 74, 74' | teeth |
| 75 | spline |
| 76 | slot |

| Reference numerals | |
|---|---|
| 77 | clicker arm |
| 78 | cut-out |
| 80 | trigger spring |
| 90 | prism |
| 100 | number wheel (display) |
| 101 | maximum stop |
| 102 | minimum stop |
| 110 | drive gear |
| 111 | spline |
| 112, 112' | teeth |
| 113 | spline teeth |
| 114 | pinion |
| 115 | ratchet |
| 116 | location feature |
| 120 | flexible piston rod |
| 121 | segment (rigid rod piece) |
| 122 | hinge |
| 123 | rack teeth |
| 124 | flange |
| 125 | foot |
| 130 | drive spring |
| 140 | cartridge |
| 141 | bung |
| 150 | cam ring |
| 151 | spline |
| 152 | saw teeth |
| 153 | spline |
| 160 | assembly tool |

The invention claimed is:

1. A drive mechanism for use in a drug delivery device having a cylindrical cartridge, the drive mechanism comprising:
a base element,
a toothed piston rod, comprising multiple rigid rod pieces comprising a first rigid rod piece comprising a circular pressure foot and a plurality of further rigid rod pieces, the toothed piston rod being guided within and movable relative to the base element, and
a drive gear having a pinion, which is rotatably held in the base element and in meshed engagement with the toothed piston rod,
wherein each of the plurality of further rigid rod pieces consists of:
a corresponding flat plate provided with a corresponding straight toothed rack, and
a corresponding flange located on an opposite side of the corresponding straight toothed rack,
wherein the corresponding flat plate together with the corresponding straight toothed rack is located offset from a center of the circular pressure foot,
wherein outer dimensions of the multiple rigid rod pieces are adapted to inner dimensions of the cylindrical cartridge such that each of the plurality of further rigid rod pieces is guided within the cylindrical cartridge by two axially extending edges of the corresponding flange and by two axially extending edges of the corresponding flat plate, and
wherein end faces of the multiple rigid rod pieces are planar, and when the toothed piston rod is straightened, adjacent faces of the multiple rigid rod pieces abut each other.

2. The drive mechanism according to claim 1, wherein the base element comprises a first curved guiding section and a second straight guiding section with the pinion of the drive gear being arranged protruding into the second straight guiding section.

3. The drive mechanism according to claim 2, wherein the second straight guiding section is located adjacent to a receiving section configured to retain the cylindrical cartridge.

4. The drive mechanism according to claim 2, wherein the base element has a generally circular configuration with the pinion being located at a center of the base element and wherein the first curved guiding section and the second straight guiding section are located offset from the center of the base element.

5. The drive mechanism according to claim 1, wherein the base element comprises a receiving section configured to retain the cylindrical cartridge.

6. The drive mechanism according to claim 1, comprising a clutch provided by a splined portion of the drive gear and a corresponding splined portion of the base element, wherein the drive gear is configured to move axially along a rotational axis of the drive gear, between a first position in which the drive gear is rotationally constrained to the base element by engagement of the clutch and a second position in which the clutch is disengaged and relative rotation between the base element and the drive gear is allowed.

7. The drive mechanism according to claim 6, comprising a compression spring interposed between the base element and the drive gear, the compression spring configured to spring bias the drive gear into the first position relative to the base element.

8. The drive mechanism according to claim 1, comprising a drive spring, which is fixed to the base element with one end and, at least when the drive gear is allowed to rotate relative to the base element, exerts a force or a torque to the drive gear for rotating the drive gear relative to the base element, which rotation results in a movement of the toothed piston rod.

9. The drive mechanism according to claim 1, wherein a length of the first rigid rod piece in an axial direction exceeds a length of each of the plurality of further rigid rod pieces in the axial direction.

10. A drug delivery device comprising:
a cartridge containing a medicament,
a drive mechanism comprising:
a base element,
a toothed piston rod, comprising multiple rigid rod pieces comprising a first rigid rod piece comprising a circular pressure foot and a plurality of further rigid rod pieces, the toothed piston rod being guided within and movable relative to the base element, and
a drive gear having a pinion, which is rotatably held in the base element and in meshed engagement with the toothed piston rod,
wherein each of the plurality of further rigid rod pieces consists of:
a corresponding flat plate provided with a corresponding straight toothed rack, and
a corresponding flange located on an opposite side of the corresponding straight toothed rack,
wherein the corresponding flat plate together with the corresponding straight toothed rack is located offset from a center of the circular pressure foot,
wherein outer dimensions of the multiple rigid rod pieces are adapted to inner dimensions of the cartridge such that each of the plurality of further rigid rod pieces is guided within the cartridge by two axially extending edges of the corresponding flange and by two axially extending edges of the corresponding flat plate, and wherein end faces of the multiple rigid rod pieces are planar, and when the toothed piston rod is straightened, adjacent faces of the multiple rigid rod pieces abut each other, a dose setting member for setting user variable doses of the medicament, a display for indicating a dose set by the dose setting member, and a coupling member interposed between the drive gear and the dose setting member.

11. The drug delivery device according to claim 10 comprising a housing rigidly fixed with the base element, the housing having a longitudinal axis defined by a compartment for receiving the cartridge containing the medicament, wherein the dose setting member is configured to rotate within the housing with an axis of rotation perpendicular to the longitudinal axis of the housing.

12. The drug delivery device according to claim 11, comprising a trigger configured to move axially in a direction of the axis of rotation of the dose setting member, wherein actuation of the trigger results in an axial movement of the drive gear and the coupling member for rotationally decoupling the drive gear and the base element.

13. The drug delivery device according to of claim 10, wherein rotation of one or more of the dose setting member, the coupling member, or the display is limited by rotational stops defining a minimum dose position and a maximum dose position.

14. The drug delivery device according to claim 10, comprising a feedback mechanism configured to generate an audible and/or tactile feedback at an end of a dose dispensing operation, the feedback mechanism comprising a ramp feature on one of the base element and the coupling member, and a flexible clicker arm on the other of the base element and the coupling member, wherein the coupling member is configured to move axially along an axis of rotation of the dose setting member, between a dose setting and dose correcting position and a dose dispensing position.

15. The drug delivery device, according to claim 10, comprising a housing having a longitudinal axis defined by a compartment configured to receive the cartridge containing the medicament, and a dose setting and drive mechanism for driving the toothed piston rod with component parts rotating about a second axis during a dose setting operation and/or a dose dispensing operation, wherein the second axis is perpendicular to the longitudinal axis of the housing, and wherein the dose setting and drive mechanism comprises a drive spring configured to exert a force or a torque for driving the toothed piston rod during the dose dispensing operation.

* * * * *

SEQUENCE LISTING

<160> NUMBER OF SEQ ID NOS: 41

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 41
<212> TYPE: PRT
<213> ORGANISM: Artificial Sequence
<220> FEATURE:
<223> OTHER INFORMATION: H-(Lys)4-des Pro36, des Pro37
      Exendin-4(1-39)-NH2

<400> SEQUENCE: 2

Lys Lys Lys Lys His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Ser
        35                  40

<210> SEQ ID NO 3

```
<211> LENGTH: 42
<212> TYPE: PRT
<213> ORGANISM: Artificial Sequence
<220> FEATURE:
<223> OTHER INFORMATION: H-(Lys)5-des Pro36, des Pro37
      Exendin-4(1-39)-NH2

<400> SEQUENCE: 3

Lys Lys Lys Lys Lys His Gly Glu Gly Thr Phe Thr Ser Asp Leu Ser
1               5                   10                  15

Lys Gln Met Glu Glu Glu Ala Val Arg Leu Phe Ile Glu Trp Leu Lys
            20                  25                  30

Asn Gly Gly Pro Ser Ser Gly Ala Pro Ser
        35                  40

<210> SEQ ID NO 4
<211> LENGTH: 38
<212> TYPE: PRT
<213> ORGANISM: Artificial Sequence
<220> FEATURE:
<223> OTHER INFORMATION: des Pro36 Exendin-4(1-39)

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 38
<212> TYPE: PRT
<213> ORGANISM: Artificial Sequence
<220> FEATURE:
<223> OTHER INFORMATION: des Pro36 [Asp28] Exendin-4(1-39)

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: des Pro36 [IsoAsp28] Exendin-4(1-39)
<220> FEATURE:
<221> NAME/KEY: MOD_RES
<222> LOCATION: (28)..(28)
<223> OTHER INFORMATION: X = isoaspartate

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35
```

```
<210> SEQ ID NO 7
<211> LENGTH: 38
<212> TYPE: PRT
<213> ORGANISM: Artificial Sequence
<220> FEATURE:
<223> OTHER INFORMATION: des Pro36 [Met(O)14, Asp28] Exendin-4(1-39)
<220> FEATURE:
<221> NAME/KEY: MOD_RES
<222> LOCATION: (14)..(14)
<223> OTHER INFORMATION: X = methionine oxide

<400> SEQUENCE: 7

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 8
<211> LENGTH: 38
<212> TYPE: PRT
<213> ORGANISM: Artificial Sequence
<220> FEATURE:
<223> OTHER INFORMATION: des Pro36 [Met(O)14, IsoAsp28] Exendin-4(1-39)
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (28)..(28)
<223> OTHER INFORMATION: X = isoaspartate

<400> SEQUENCE: 8

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 9
<211> LENGTH: 38
<212> TYPE: PRT
<213> ORGANISM: Artificial Sequence
<220> FEATURE:
<223> OTHER INFORMATION: des Pro36 [Trp(O2)25, Asp28] Exendin-4(1-39)
<220> FEATURE:
<221> NAME/KEY: MOD_RES
<222> LOCATION: (25)..(25)
<223> OTHER INFORMATION: X = tryptophan dioxide

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Artificial Sequence
<220> FEATURE:
```

```
<223> OTHER INFORMATION: des Pro36 [Trp(O2)25, IsoAsp28] Exendin-4(1-39)
<220> FEATURE:
<221> NAME/KEY: MOD_RES
<222> LOCATION: (25)..(25)
<223> OTHER INFORMATION: X=tryptophan dioxide
<220> FEATURE:
<221> NAME/KEY: MOD_RES
<222> LOCATION: (28)..(28)
<223> OTHER INFORMATION: X=isoaspartate

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 11
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, Asp28]
      Exendin-4(1-39)
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (25)..(25)
<223> OTHER INFORMATION: X = tryptophan dioxide

<400> SEQUENCE: 11

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 12
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, IsoAsp28]
      Exendin-4(1-39)
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (25)..(25)
<223> OTHER INFORMATION: X = tryptophan dioxide
<220> FEATURE:
<221> NAME/KEY: MOD_RES
<222> LOCATION: (28)..(28)
<223> OTHER INFORMATION: X = isoaspartate

<400> SEQUENCE: 12

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
```

-continued

```
<210> SEQ ID NO 13
<211> LENGTH: 44
<212> TYPE: PRT
<213> ORGANISM: Artificial Sequence
<220> FEATURE:
<223> OTHER INFORMATION: des Pro36 Exendin-4(1-39)-Lys6-NH2

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 14
<211> LENGTH: 50
<212> TYPE: PRT
<213> ORGANISM: Artificial Sequence
<220> FEATURE:
<223> OTHER INFORMATION: H-(Lys)6-des Pro36 [Asp28]
      Exendin-4(1-39)-Lys6-NH2

<400> SEQUENCE: 14

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 15
<211> LENGTH: 38
<212> TYPE: PRT
<213> ORGANISM: Artificial Sequence
<220> FEATURE:
<223> OTHER INFORMATION: des Asp28 Pro36, Pro37,
      Pro38Exendin-4(1-39)-NH2

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
            20                  25                  30

Gly Ala Pro Pro Pro Ser
        35

<210> SEQ ID NO 16
<211> LENGTH: 44
<212> TYPE: PRT
<213> ORGANISM: Artificial Sequence
<220> FEATURE:
<223> OTHER INFORMATION: H-(Lys)6-des Pro36, Pro38 [Asp28]
      Exendin-4(1-39)-NH2

<400> SEQUENCE: 16

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
```

```
                    20                  25                  30

Lys Asp Gly Gly Pro Ser Ser Gly Ala Pro Pro Ser
            35                  40

<210> SEQ ID NO 17
<211> LENGTH: 44
<212> TYPE: PRT
<213> ORGANISM: Artificial Sequence
<220> FEATURE:
<223> OTHER INFORMATION: H-Asn-(Glu)5des Pro36, Pro37, Pro38 [Asp28]
      Exendin-4(1-39)-NH2

<400> SEQUENCE: 17

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
            35                  40

<210> SEQ ID NO 18
<211> LENGTH: 44
<212> TYPE: PRT
<213> ORGANISM: Artificial Sequence
<220> FEATURE:
<223> OTHER INFORMATION: des Pro36, Pro37, Pro38 [Asp28]
      Exendin-4(1-39)-(Lys)6-NH2

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 19
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Asp28]
      Exendin-4(1-39)-(Lys)6-NH2

<400> SEQUENCE: 19

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
            35                  40                  45

Lys Lys
    50

<210> SEQ ID NO 20
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Asp28]
      Exendin-4(1-39)-(Lys)6-NH2

<400> SEQUENCE: 20
```

```
Asn Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 21
<211> LENGTH: 50
<212> TYPE: PRT
<213> ORGANISM: Artificial Sequence
<220> FEATURE:
<223> OTHER INFORMATION: H-(Lys)6-des Pro36 [Trp(O2)25, Asp28]
      Exendin-4(1-39)-Lys6-NH2
<220> FEATURE:
<221> NAME/KEY: MOD_RES
<222> LOCATION: (31)..(31)
<223> OTHER INFORMATION: X = tryptophan dioxide

<400> SEQUENCE: 21

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 22
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Trp(O2)25]
      Exendin-4(1-39)-NH2
<220> FEATURE:
<221> NAME/KEY: MOD_RES
<222> LOCATION: (25)..(25)
<223> OTHER INFORMATION: X = tryptophan dioxide

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Gly Gly Pro Ser Ser
            20                  25                  30

Gly Ala Pro Pro Pro Ser
        35

<210> SEQ ID NO 23
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-NH2
<220> FEATURE:
<221> NAME/KEY: MOD_RES
<222> LOCATION: (31)..(31)
<223> OTHER INFORMATION: X = tryptophan dioxide

<400> SEQUENCE: 23

Lys Lys Lys Lys Lys Lys His Gly Glu Gly Thr Phe Thr Ser Asp Leu
```

```
                1               5                   10                  15
Ser Lys Gln Met Glu Glu Glu Ala Val Arg Leu Phe Ile Glu Xaa Leu
                    20                  25                  30

Lys Asp Gly Gly Pro Ser Ser Gly Ala Pro Pro Ser
                35                  40
```

<210> SEQ ID NO 24
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-NH2
<220> FEATURE:
<221> NAME/KEY: MOD_RES
<222> LOCATION: (31)..(31)
<223> OTHER INFORMATION: X = tryptophan dioxide

<400> SEQUENCE: 24

```
Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
                    20                  25                  30

Lys Asp Gly Gly Pro Ser Ser Gly Ala Pro Pro Ser
                35                  40
```

<210> SEQ ID NO 25
<211> LENGTH: 44
<212> TYPE: PRT
<213> ORGANISM: Artificial Sequence
<220> FEATURE:
<223> OTHER INFORMATION: des Pro36, Pro37, Pro38 [Trp(O2)25, Asp28]
      Exendin-4(1-39)-(Lys)6-NH2
<220> FEATURE:
<221> NAME/KEY: MOD_RES
<222> LOCATION: (25)..(25)
<223> OTHER INFORMATION: X = tryptophan dioxide

<400> SEQUENCE: 25

```
His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
                    20                  25                  30

Ser Gly Ala Pro Pro Ser Lys Lys Lys Lys Lys Lys
                35                  40
```

<210> SEQ ID NO 26
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-(Lys)6-NH2
<220> FEATURE:
<221> NAME/KEY: MOD_RES
<222> LOCATION: (31)..(31)
<223> OTHER INFORMATION: X = tryptophan dioxide

<400> SEQUENCE: 26

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
                    20                  25                  30

Lys Asp Gly Gly Pro Ser Ser Gly Ala Pro Pro Ser Lys Lys Lys Lys
                35                  40                  45
```

```
Lys Lys
    50

<210> SEQ ID NO 27
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-(Lys)6-NH2
<220> FEATURE:
<221> NAME/KEY: MOD_RES
<222> LOCATION: (31)..(31)
<223> OTHER INFORMATION: X = tryptophan dioxide

<400> SEQUENCE: 27

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 28
<211> LENGTH: 50
<212> TYPE: PRT
<213> ORGANISM: Artificial Sequence
<220> FEATURE:
<223> OTHER INFORMATION: H-(Lys)6-des Pro36 [Met(O)14, Asp28]
      Exendin-4(1-39)-Lys6-NH2
<220> FEATURE:
<221> NAME/KEY: MOD_RES
<222> LOCATION: (20)..(20)
<223> OTHER INFORMATION: X = methionine oxide

<400> SEQUENCE: 28

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 29
<211> LENGTH: 38
<212> TYPE: PRT
<213> ORGANISM: Artificial Sequence
<220> FEATURE:
<223> OTHER INFORMATION:
      KKKKKKHGEGTFTSDLSKQXEEEAVRLFIEWLKDGGPSSGAPPSKKKKKK

<400> SEQUENCE: 29

His Gly Glu Gly Thr Phe Thr Ser Asp Leu Ser Lys Gln Glu Glu Glu
1               5                   10                  15

Ala Val Arg Leu Phe Ile Glu Trp Leu Lys Asp Gly Gly Pro Ser Ser
            20                  25                  30

Gly Ala Pro Pro Pro Ser
        35
```

```
<210> SEQ ID NO 30
<211> LENGTH: 44
<212> TYPE: PRT
<213> ORGANISM: Artificial Sequence
<220> FEATURE:
<223> OTHER INFORMATION: H-(Lys)6-desPro36, Pro37, Pro38 [Met(O)14,
      Asp28] Exendin-4(1-39)-NH2
<220> FEATURE:
<221> NAME/KEY: MOD_RES
<222> LOCATION: (20)..(20)
<223> OTHER INFORMATION: X = methionine oxide

<400> SEQUENCE: 30

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
            35                  40

<210> SEQ ID NO 31
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38
      [Met(O)14, Asp28] Exendin-4(1-39)-NH2
<220> FEATURE:
<221> NAME/KEY: MOD_RES
<222> LOCATION: (20)..(20)
<223> OTHER INFORMATION: X = methionine oxide

<400> SEQUENCE: 31

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
            35                  40

<210> SEQ ID NO 32
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Asp28]
      Exendin-4(1-39)-(Lys)6-NH2
<220> FEATURE:
<221> NAME/KEY: MOD_RES
<222> LOCATION: (14)..(14)
<223> OTHER INFORMATION: X = methionine oxide

<400> SEQUENCE: 32

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 33
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Asp28] Exendin-4(1-39)-(Lys)6-NH2
```

```
<220> FEATURE:
<221> NAME/KEY: MOD_RES
<222> LOCATION: (20)..(20)
<223> OTHER INFORMATION: X = methionine oxide

<400> SEQUENCE: 33

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 34
<211> LENGTH: 50
<212> TYPE: PRT
<213> ORGANISM: Artificial Sequence
<220> FEATURE:
<223> OTHER INFORMATION: H-Asn-(Glu)5 des Pro36, Pro37, Pro38 [Met(O)14,
      Asp28] Exendin-4(1-39)-(Lys)6-NH2
<220> FEATURE:
<221> NAME/KEY: MOD_RES
<222> LOCATION: (20)..(20)
<223> OTHER INFORMATION: X = methionine oxide

<400> SEQUENCE: 34

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 35
<211> LENGTH: 50
<212> TYPE: PRT
<213> ORGANISM: Artificial Sequence
<220> FEATURE:
<223> OTHER INFORMATION: H-Lys6-des Pro36 [Met(O)14, Trp(O2)25, Asp28]
      Exendin-4(1-39)-Lys6-NH2
<220> FEATURE:
<221> NAME/KEY: MOD_RES
<222> LOCATION: (20)..(20)
<223> OTHER INFORMATION: X = methionine oxide
<220> FEATURE:
<221> NAME/KEY: MOD_RES
<222> LOCATION: (31)..(31)
<223> OTHER INFORMATION: X = tryptophan dioxide

<400> SEQUENCE: 35

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 36
```

```
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Met(O)14,
      Trp(O2)25] Exendin-4(1-39)-NH2
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (24)..(24)
<223> OTHER INFORMATION: X = tryptophan oxide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 36

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Gly Gly Pro Ser Ser
                20                  25                  30

Gly Ala Pro Pro Pro Ser
            35

<210> SEQ ID NO 37
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Asp28] Exendin-4(1-39)-NH2
<220> FEATURE:
<221> NAME/KEY: MOD_RES
<222> LOCATION: (20)..(20)
<223> OTHER INFORMATION: X = methionine oxide

<400> SEQUENCE: 37

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
                20                  25                  30

Lys Asp Gly Gly Pro Ser Ser Gly Ala Pro Pro Ser
            35                  40

<210> SEQ ID NO 38
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-NH2
<220> FEATURE:
<221> NAME/KEY: MOD_RES
<222> LOCATION: (20)..(20)
<223> OTHER INFORMATION: X = methionine oxide
<220> FEATURE:
<221> NAME/KEY: MOD_RES
<222> LOCATION: (31)..(31)
<223> OTHER INFORMATION: X = tryptophan oxide

<400> SEQUENCE: 38

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
                20                  25                  30
```

-continued

```
Lys Asp Gly Gly Pro Ser Ser Gly Ala Pro Pro Ser
        35                  40

<210> SEQ ID NO 39
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Trp(O2)25,
      Asp28] Exendin-4(1-39)-(Lys)6-NH2
<220> FEATURE:
<221> NAME/KEY: MOD_RES
<222> LOCATION: (14)..(14)
<223> OTHER INFORMATION: X = methionine oxide
<220> FEATURE:
<221> NAME/KEY: MOD_RES
<222> LOCATION: (25)..(25)
<223> OTHER INFORMATION: X = tryptophan oxide

<400> SEQUENCE: 39

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
        35                  40

<210> SEQ ID NO 40
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Trp(O2)25, Asp28] Exendin-4(S1-39)-(Lys)6-NH2
<220> FEATURE:
<221> NAME/KEY: MOD_RES
<222> LOCATION: (20)..(20)
<223> OTHER INFORMATION: X = methionine oxide
<220> FEATURE:
<221> NAME/KEY: MOD_RES
<222> LOCATION: (31)..(31)
<223> OTHER INFORMATION: X = tryptophan oxide

<400> SEQUENCE: 40

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 41
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-(Lys)6-NH2
<220> FEATURE:
<221> NAME/KEY: MOD_RES
<222> LOCATION: (20)..(20)
<223> OTHER INFORMATION: X = methionine oxide
<220> FEATURE:
<221> NAME/KEY: MOD_RES
<222> LOCATION: (31)..(31)
<223> OTHER INFORMATION: X = tryptophan oxide
```

```
<400> SEQUENCE: 41

Asn Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50
```

UNITED STATES PATENT AND TRADEMARK OFFICE
CERTIFICATE OF CORRECTION

PATENT NO. : 10,918,799 B2  
APPLICATION NO. : 15/532795  
DATED : February 16, 2021  
INVENTOR(S) : William Geoffrey Arthur Marsh and Matthew Meredith Jones Page 1 of 1

It is certified that error appears in the above-identified patent and that said Letters Patent is hereby corrected as shown below:

In the Claims

In Column 49, Line 21, Claim 1, delete "rod," and insert -- rod --

In Column 50, Line 46, Claim 10, delete "rod," and insert -- rod --

In Column 51, Line 26, Claim 13, after "to" delete "of"

In Column 52, Line 15, Claim 15, delete "device," and insert -- device --

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*